(12) United States Patent
Hershey et al.

(10) Patent No.: US 12,303,113 B2
(45) Date of Patent: *May 20, 2025

(54) NON-INVASIVE METHODS FOR SKIN SAMPLE COLLECTION AND ANALYSIS

(71) Applicant: CHILDREN'S HOSPITAL MEDICAL CENTER, Cincinnati, OH (US)

(72) Inventors: Gurjit Khurana Hershey, Cincinnati, OH (US); Jocelyn Biagini-Myers, Cincinnati, OH (US); Eric Schauberger, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/435,217

(22) Filed: Feb. 7, 2024

(65) Prior Publication Data

US 2024/0173019 A1    May 30, 2024

Related U.S. Application Data

(62) Division of application No. 16/490,438, filed as application No. PCT/US2018/020816 on Mar. 3, 2018, now Pat. No. 11,911,012.

(Continued)

(51) Int. Cl.
*A61B 10/02*       (2006.01)
*C12Q 1/6888*      (2018.01)

(52) U.S. Cl.
CPC ............ *A61B 10/02* (2013.01); *C12Q 1/6888* (2013.01); *A61B 2503/06* (2013.01)

(58) Field of Classification Search
None
See application file for complete search history.

(56) References Cited

U.S. PATENT DOCUMENTS

| 5,325,864 A | 7/1994 | Gerber |
|---|---|---|
| 8,690,792 B2 | 4/2014 | Horsewood et al. |

(Continued)

FOREIGN PATENT DOCUMENTS

| JP | H04-121664 A | 4/1992 |
|---|---|---|
| JP | H09-84796 A | 1/1997 |

(Continued)

OTHER PUBLICATIONS

Drury, Ruth E. et al., The Clinical Application of MicroRNAs in Infectious Disease, Frontiers in Immunology, vol. 8, Article 1182, pp. 1-17 (Sep. 2017).

*Primary Examiner* — Jay B Shah
(74) *Attorney, Agent, or Firm* — Porter Wright Morris & Arthur LLP

(57) ABSTRACT

Kits for assessing a skin condition of a subject comprise (a) a first set of adhesive tapes adapted to adhere a first biological material from stratum corneum of a target skin site of the subject, (b) a second set of adhesive tapes adapted to adhere a second biological material from an epidermis layer below stratum corneum of a target skin site of the subject, wherein each of the adhesive tapes in the first set of adhesive tapes and the second set of adhesive tapes comprises a water-soluble adhesive layer attached to a substrate, (c) one or more reagents for extracting biological material adhered to the water-soluble adhesive layers of the adhesive tapes, and (d) one or more detection agents for determining a presence of microbial biological materials and/or host biological materials from water-soluble adhesive tape extract.

20 Claims, 22 Drawing Sheets

Specification includes a Sequence Listing.

Related U.S. Application Data

(60) Provisional application No. 62/466,667, filed on Mar. 3, 2017.

(56) References Cited

U.S. PATENT DOCUMENTS

| | | |
|---|---|---|
| 2002/0182149 A1 | 12/2002 | Telesca et al. |
| 2007/0281314 A1 | 12/2007 | Benson |

FOREIGN PATENT DOCUMENTS

| | | |
|---|---|---|
| JP | H09-243636 A | 9/1997 |
| JP | 2003-344390 A | 12/2003 |
| JP | 2007003413 A | 1/2007 |
| JP | 2008-97 A | 1/2008 |
| JP | 2012-177601 A | 9/2012 |
| JP | 2016-19531 A | 2/2016 |
| WO | 2006/002967 A1 | 1/2006 |
| WO | 2008/086596 A1 | 7/2008 |

| Peak | Size (bp) | Conc. (ng/uL) | From (bp) | To (bp) | Avg. Size (bp) | CV% | RFU | Corr. Peak Area |
|---|---|---|---|---|---|---|---|---|
| 1 | 1 (LM) | 0.0126 | 0 | 10 | — | 104.11 | 835 | 4.053 |
| 2 | 35 | 0.3993 | 10 | 122 | 42 | 35.23 | 842 | 10.865 |
| 3 | 210 | 1.5981 | 138 | 526 | 298 | 30.28 | 206 | 42.883 |
| 4 | 1113 | 0.1831 | 830 | 4315 | 1304 | 41.20 | 69 | 4.630 |
| 5 | 8000 (UM) | 0.0055 | 5485 | 8419 | 5883 | 1.79 | 499 | 2.068 |

| | | | |
|---|---|---|---|
| TIC: | 2.1806 | ng/uL | |
| TIM: | 29.049 | nmole/L | |
| Total Conc.: | 2.4196 | ng/uL | |

| Smear Analysis | 250 bp to 600 bp | 1.0758 ng/uL | 44.5% Total | 4.823 nmole/L | 367 Avg. Size (b.p.) | 25.08 %CV |
|---|---|---|---|---|---|---|

Figure 10 continued

| Peak | Size (bp) | Conc. (ng/uL) | From (bp) | To (bp) | Avg. Size (bp) | CV% | RFD | Corr. Peak Area |
|---|---|---|---|---|---|---|---|---|
| 1 | 1 (LM) | 0.0128 | 0 | 11 | – | 178.61 | 593 | 3,040 |
| 2 | 40 | 0.7214 | 11 | 124 | 45 | 20.95 | 838 | 14,455 |
| 3 | 198 | 2.8156 | 133 | 983 | 309 | 39.25 | 283 | 56,415 |
| 4 | 6000 (UM) | 0.0050 | 5663 | 8865 | 5986 | 2.15 | 275 | 1,214 |
| TIC: | | 3.5370 | ng/uL | | | | | |
| TIM: | | 52.796 | nmole/L | | | | | |
| Total Conc.: | | 3.5698 | ng/uL | | | | | |

| Smear Analysis | 250 bp to 500 bp | 1.6236 ng/uL | 45.5% total | 7.627 nmole/L | 350 Avg. Size (b.p.) | 23.76 %CV |
|---|---|---|---|---|---|---|

Figure 10 continued

| Peak | Size (bp) | Conc. (ng/uL) | From (bp) | To (bp) | Avg. Size (bp) | CV% | RFU | Corr. Peak Area |
|---|---|---|---|---|---|---|---|---|
| 1 | 1 (LM) | 0.0128 | 0 | 9 | — | 183.04 | 500 | 2,938 |
| 2 | 41 | 2.5972 | 0 | 130 | 47 | 33.99 | 3643 | 50,295 |
| 3 | 218 | 7.2187 | 144 | 755 | 323 | 37.37 | 847 | 139,788 |
| 4 | 8000 (UM) | 0.0064 | 5232 | 6906 | 5871 | 2.01 | 341 | 1,478 |

| | | |
|---|---|---|
| TIC | 9.8159 | ng/uL |
| TIM | 158.206 | nmole/L |
| Total Conc. | 10.0848 | ng/uL |

| Smear Analysis | 250 bp to 800 bp | 4.5060 ng/uL | 44.7% Total | 20.626 nmole/L | 390 Avg. Size (b.p.) | 24.49 %CV |
|---|---|---|---|---|---|---|

*Figure 10 continued*

| Peak | Size (bp) | Conc. (ng/uL) | From (bp) | To (bp) | Avg. Size (bp) | CV% | RFU | Corr. Peak Area |
|---|---|---|---|---|---|---|---|---|
| 1 | 1 (LM) | 0.0125 | 0 | 14 | 2 | 167.35 | 287 | 1.779 |
| 2 | 41 | 0.4267 | 26 | 97 | 47 | 24.03 | 347 | 5.003 |
| 3 | 243 | 0.7123 | 154 | 283 | 231 | 12.63 | 78 | 8.353 |
| 4 | 8000 (UM) | 0.0064 | 5628 | 7183 | 5997 | 2.50 | 205 | 0.898 |

| | | |
|---|---|---|
| TIC: | 1.1580 | ng/uL |
| TIM: | 21.6632 | nmole/L |
| Total Conc.: | 1.9234 | ng/uL |

Smear Analysis  250 bp to 600 bp  0.9160 ng/uL  47.5% Total  4.289 nmole/L  351 Avg. Size (b.p.)  23.47 %CV

Figure 10 continued

NON-INVASIVE METHODS FOR SKIN SAMPLE COLLECTION AND ANALYSIS

CROSS-REFERENCE TO RELATED APPLICATIONS

This application claims the benefit under 35 U.S.C. § 119(e) of U.S. provisional application No. 62/466,667, filed Mar. 3, 2017, the contents of which are incorporated by reference herein in their entirety, and the benefit under 35 U.S.C. § 120 of U.S. application Ser. No. 16/490,438 filed Aug. 30, 2019, the contents of which are incorporated by reference herein in their entirety, and which is a 371 of PCT/US2018/020816 filed Mar. 3, 2018.

GOVERNMENT SUPPORT

This invention was made with government support under Contract No. NIH NIAID 2U19AI070235, and NIH NIAID T32AI60515 awarded by National Institutes of Health. The government has certain rights in the invention.

SEQUENCE LISTING

The Sequence Listing submitted herewith, entitled "Feb-20-2024-Sequence-Listing.xml", created Feb. 20, 2024, and having a size of 3462 bytes, is incorporated herein by reference.

BACKGROUND

Skin samples can be used for studying the molecular underpinnings of skin diseases. However, understanding and optimal management of many complex skin diseases, such as atopic dermatitis, have been limited by a lack of reliable and non-invasive methods to collect skin samples for developing clinically useful biomarkers of skin conditions that can aid diagnosis, and/or guide the selection of appropriate treatment strategy.

While a skin biopsy is a common clinical tool for diagnostic purposes, it may not be feasible for use with individuals (with or without skin diseases) in biomarker determination and/or research due to a number of factors, including, e.g., the risks associated with an inherently invasive procedure, the need for local anesthesia, the time required, and the need for trained staff. These risks are even less justifiable in subjects (e.g., subjects without a skin disease) who otherwise have no reason to undergo the procedure.

Several methods for minimally invasive skin collection have emerged over the past years. Examples of such methods include, e.g., sampling with Q-tips or gauzes, abrasion techniques, reverse iontophoresis, and ultrasound-based methods. There is still a need for developing non-invasive methods that would enable simultaneous sampling of the skin surface with the layers below the skin surface such that biologic connections between the skin surface and the pathways induced in the epidermis can be investigated to determine clinically relevant skin biomarkers and to gain a molecular understanding of skin diseases.

SUMMARY OF THE INVENTION

The present disclosure is, at least in part, based on the development of a robust, low cost method, and minimally invasive method for collecting skin samples. The method described herein involves the use of multiple water-soluble adhesive tapes for sequential collection of skin samples at the same skin site. Unexpectedly, the method described herein enables simultaneous sampling of the skin surface with the layers below such that the biologic connections between the surface and the pathways induced in the epidermis could be investigated. For example, the method allows for simultaneous collection of various biological materials from a single skin site, e.g., microbiome, epidermal DNA, epidermal RNA and epidermal lipids, which can be used individually or together to examine molecular signatures of disease in the keratinocytes (e.g., epigenetics, transcriptomics, and genetics). This simultaneous sampling of the skin surface and epidermal layer(s) below the skin surface facilitates identification of the connections/correlations between the skin surface and molecular pathways induced in the epidermis, which can be useful, e.g., to identify molecular signatures of a disease in the keratinocytes and/or to provide a holistic analysis of a skin condition. The methods described herein have at least the advantages of being 1) noninvasive and without need for anesthesia, 2) easy to perform, 3) rapid, 4) reliable and consistent, 5) cost-effective, 6) scalable to meet the needs of collection in large cohorts, and 7) samples can be stored for later processing.

Accordingly, one aspect of the present disclosure features a non-invasive method for collecting biological materials from the skin of a subject. The method comprises (a) contacting a target skin site of a subject with each of a first set of adhesive tapes one following another, to allow a first set of biological materials from the target skin site to adhere to the first set of the adhesive tapes; and (b) contacting, after (a), the same target skin site of the subject with each of a second set of adhesive tapes one following another, to allow a second set of biological materials from the target skin site to adhere to the second set of the adhesive tapes, wherein each of the adhesive tapes in the first set and the second set comprises a water-soluble adhesive attached to a substrate. In some embodiments, the contacting (b) is performed immediately after the contacting step (a). In some embodiments, the method may further comprise (c) contacting, after (b), the same target skin site of the subject with each of a third set of adhesive tapes one following another, to allow a third set of biological materials from the target skin site to adhere to the third set of the adhesive tapes, wherein each of the adhesive tapes in the third set comprises a water-soluble adhesive layer attached to a substrate.

In another aspect, the present disclosure provides a method for determining a biological material profile of a target skin site of a subject. The method comprises: (aI) providing a first set of adhesive tapes, which comprises a first set of biological materials from a target skin site of a subject; (a2) analyzing presence of at least one microbial biological material from the first set of the biological materials; (bI) providing a second set of adhesive tapes, which comprises a second set of biological materials from the target skin site of the subject, wherein the second set of the biological materials is collected after collection of the first set of the biological materials; and (b2) analyzing presence of at least one host biological material from the second set of the biological materials; wherein each of the adhesive tapes in the first set and the second set comprises a water-soluble adhesive attached to a substrate. In some embodiments, the contacting (bI) is performed immediately after the contacting step (aI). In some embodiments, the method may further comprise (cI) providing a third set of adhesive tapes, which comprises a third set of biological materials from the target skin site of the subject, wherein the third set of the biological materials is collected after collection of the second set of the biological materials; and (c2) analyzing presence of at least one host biological material from the third set of biological materials, wherein each of the adhesive tapes in the third set comprises a water-soluble adhesive layer attached to a substrate.

In some embodiments of various aspects involving the methods described herein, each set of the adhesive tapes (e.g., the first set, the second set, and/or the third set) can independently contain 2-5 tapes.

The adhesive tapes in each set can contain the same tapes or different tapes. The adhesive tapes in each set comprise a water-soluble adhesive attached to a substrate. In some embodiments, the substrate is a solid substrate that is water soluble. For example, a water-soluble solid substrate may comprise cellulose. In some embodiments, a water-soluble adhesive may comprise a water-soluble polymer, e.g., but not limited to a water-soluble acrylic polymer.

The adhesive tapes can be applied to a subject at any age. For example, the adhesive tapes can be applied to a subject at any age who has a skin disease or disorder (e.g., atopic dermatitis). In some embodiments, the subject can be a child. In some embodiments, the subject can be an adult.

The adhesive tapes can be applied to a target skin site anywhere on the skin of the subject, e.g., a skin site at which an analysis of a skin condition is needed. For example, a target skin site may be on the ankle, arm (e.g., upper arm or forearm), behind the ear, between fingers, back of the neck, upper back or lower back, legs, waist. In some embodiments, a target skin site is on the forearm. In some embodiments, the target skin site is substantially void of hair. In some embodiments, the target skin site may comprise a lesional site. In some embodiments, the target skin site may be a non-lesional site.

Each set of the adhesive tapes collects a set of biological materials from the target skin site of a subject. For example, the first set of the biological materials may comprise biological materials from stratum corneum of the subject. In some embodiments, the presence of microbial biological materials in the first set of the biological materials can be determined. For example, the presence of biological materials (e.g., cells, polypeptides, nucleic acids, lipids, small molecules, etc.) from bacteria, virus, yeast, and/or fungus collected in the first set of the biological materials can be analyzed. In some embodiments, microbial cells isolated from the first set of the biological materials can be subjected to culturing, e.g., for propagation. In some embodiments, microbial nucleic acids from the first set of the biological materials can be amplified and the amplified nucleic acids can be analyzed.

In some embodiments, the second and/or third set of the biological materials may comprise biological materials from an epidermis layer below stratum corneum of the subject. In some embodiments, the presence of host biological materials from the second and/or third sets of the biological materials can be determined. For example, the presence of biological materials (e.g., cells, polypeptides, nucleic acids, lipids, small molecules, etc.) from keratinocytes collected in the second and/or third sets of the biological materials can be analyzed. In some embodiments, keratinocyte nucleic acids from the second and/or third sets of the biological materials can be amplified and the amplified nucleic acids can be analyzed.

In some embodiments, any one of the first, second, and third sets of the biological materials can be analyzed to determine the presence of at least one or more lipids.

Also within the scope of the present disclosure are kits for assessing skin condition of a subject. For example, in one aspect, the kit comprises: (a) one or more reagents for extracting biological materials adhered to water-soluble adhesive tapes; and (b) one or more detection agents for determining presence of microbial biological materials and/or host biological materials. In some embodiments, the kit can further comprise a plurality of water-soluble adhesive tapes. In some embodiments, the detection agent(s) provided in the kit may comprise a microbial culture medium, agents for detecting microorganisms, agents for detecting host biological materials, or a combination thereof.

The details of one or more embodiments of the disclosure are set forth in the description below. Other features or advantages of the present disclosure will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 6A shows a representative bubble plot of a single tape strip taken from healthy adult controls (n=12). FIG. 6B shows a representative bubble plot of a single tape strip taken from non-lesional and lesional sites of atopic dermatitis patients (n=12). Library preparation and sequencing were done using Illumina NextSeq 550 sequencer and Tableau was used for analysis. Number of individual circles in bubble plots represent species diversity and bubble size indicates abundance. The tape strip method provides a sufficient amount of quality bacterial DNA for library preparation, sequencing, and metagenomic analysis.

DETAILED DESCRIPTION

Figure 1:
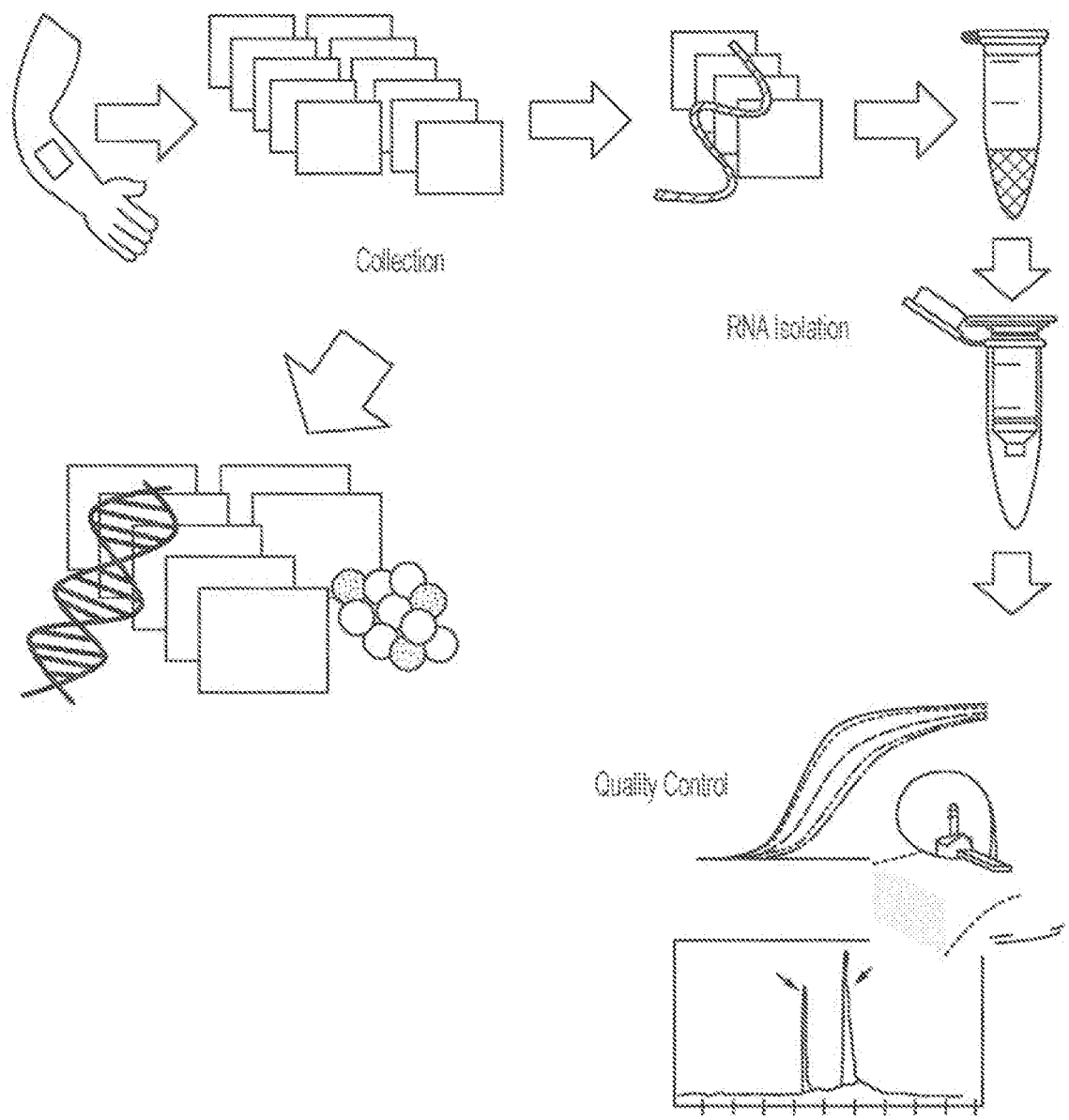
FIG. 1 is a schematic diagram showing an exemplary non-invasive process for collecting biological materials from skin for microbiome, DNA, and RNA analyses.

There is a lack of rapid and reliable minimally-invasive tools/methods to collect biological materials from skin for biomarker identification as well as for mechanistic, epigenetic, and genomic studies, e.g., for dermatologic diseases. Skin biopsies have been commonly used but require highly-trained healthcare providers, and are invasive, time-consuming, and impractical for collection in large cohorts. Accordingly, there is a need to develop a cost-effective, minimally-invasive, reliable, sensitive, and scalable toolkit and/or method for simultaneous collection of biological materials to assess the skin microbiome and host biological materials {e.g., keratinocyte biological materials).

The present disclosure is, at least in part, based on the development of a robust, cost-effective, and minimally invasive method for collecting skin samples. The method described herein involves the use of multiple water-soluble adhesive tapes for sequential collection of skin samples at the same skin site. Unexpectedly, the method described herein enables simultaneous sampling of the skin surface with the epidermal layers below the skin surface such that the biologic connections between the skin surface and the cellular/molecular pathways induced in the epidermis could be investigated. For example, it was shown that the method allows simultaneous collection of at least microbial nucleic acids and keratinocyte nucleic acids from a single skin site of patients with atopic dermatitis (AD), who are known to have low amounts of nucleic acids present in the skin. Further, it was shown that use of water-soluble adhesive tapes significantly improved the yields of biological materials {e.g., nucleic acids) collected from a skin site, as compared to using water-insoluble adhesive tapes. Thus, the methods described herein effectively allows for simultaneous collection of various biological materials from a single skin site, e.g., microbiome, epidermal DNA, epidermal RNA and epidermal lipids, which, for example, can be used individually or together to examine or identify molecular signatures of a disease in the keratinocytes {e.g., epigenetics, transcriptomics, and genetics) and/or to provide a holistic analysis of a skin condition. The methods described herein have at least the following advantages of being 1) non-invasive and without need for anesthesia, 2) easy to perform, 3) rapid, 4) reliable and consistent, 5) cost-effective, 6) scalable to meet the needs of collection in large cohorts, and 7) allowing samples to be stored for later processing.

Accordingly, described herein are methods and kits for collecting and/or detecting biological materials from the skin of a subject using multiple water-soluble adhesive tapes for collecting skin sample sequentially (one following another) at the same skin site. In some embodiments, skin samples collected by the first several adhesive tapes (the first set) can be used for analyzing presence of microbial biological material(s) while skin samples collected by the subsequent tapes (the second set and optionally the third set) can be used for analyzing host biological material(s) from an epidermal layer below the skin surface. The methods and kits described herein can enable assessment of skin microbiome and host keratinocyte-associated biological materials (e.g., nucleic acids) at the same target skin site such that molecular/biological connections/correlations between the microbiome and skin surface and cellular/molecular pathways induced in the epidermal layer(s) below the skin surface can be explored and investigated.

In some aspects, the disclosure relates to methods for collecting biological materials from the skin of a subject. In some embodiments, the methods comprise: (a) contacting a target skin site of a subject with each of a first set of adhesive tapes one following another, to allow a first set of biological materials from the target skin site to adhere to the first set of the adhesive tapes; and (b) contacting, after (a), the same target skin site of the subject with each of a second set of adhesive tapes one following another, to allow a second set of biological materials from the target skin site to adhere to the second set of the adhesive tapes; wherein each of the adhesive tapes in the first set and the second set comprises a water-soluble adhesive layer attached to a substrate.

In other aspects, the disclosure relates to methods for determining a biological material profile of a target skin site of a subject. In some embodiments, the methods comprise: (a1) providing a first set of adhesive tapes, which comprises a first set of biological materials from a target skin site of a subject; (a2) analyzing presence of at least one microbial biological material from the first set of the biological materials; (b1) providing a second set of adhesive tapes, which comprises a second set of biological materials from the target skin site of the subject, wherein the second set of the biological materials is collected after collection of the first set of the biological materials; and (b2) analyzing presence of at least one host biological material from the second set of the biological materials; wherein each of the adhesive tapes in the first set and the second set comprises a water-soluble adhesive layer attached to a substrate.

In any of the methods described herein, a third set of adhesive tapes can be provided or used to collect a third set of biological materials from the same target skin site of the subject, wherein the third set of the adhesive tapes is applied after the second set of the adhesive tapes is applied and removed from the target skin site. At least one biological material from the third set can then be analyzed. If necessary, additional set(s) of adhesive tapes can be provided or used after a third set of adhesive tapes to collect an additional set of biological materials from the same target skin site of the subject.

I. Water-Soluble Adhesives Tapes for Collecting Biological Materials from Target Skin Sites Adhesive tapes in each set (e.g., first set, second set, and/or third set) used for collecting skin samples in any of the methods described herein are water-soluble adhesive tapes comprising a water-soluble adhesive attached to a solid substrate, which may also be water soluble. In some embodiments, the adhesive tapes in each set can be the same tapes. In some embodiments, the adhesive tapes in each set can be different, e.g., depending on the types of biological materials to be collected.

A water-soluble adhesive is dissolvable in water and/or in an aqueous buffer solution. The aqueous buffer solution can comprise a buffer agent (e.g., but not limited to Tris or tris(hydroxymethyl)aminomethane), a polyol (e.g., glycerol or derivative thereof, such as thioglycerol), and/or a protein denaturant (e.g., but not limited to guanidinium thiocyanate). In some embodiments, the adhesive is dissolvable in water or in an aqueous buffer solution at a neutral pH, e.g., pH 6, pH 7, or pH 8 and/or at a temperature of 4° C.-25° C. or 4° C.-10° C. In one embodiment, the adhesive is dissolvable in an aqueous buffer solution comprising guanidine thiocyanate, Tris (pH 7-8), and 1-thioglycerol at a temperature of 4° C.-10° C.

In some embodiments, the water-soluble adhesive comprises a water-soluble polymeric adhesive. Examples of such water-soluble polymeric adhesive include, but are not limited to acrylic polymers (e.g., but not limited to acrylic acid polymer or acrylic acid ester/acrylic acid copolymer), carboxymethyl starch, polyvinyl alcohol, cellulose ethers, methylcellulose, carboxymethylcellulose, polyvinylpyrrolidone, glutin adhesives, starch adhesives, casein adhesive, and any combinations thereof. In some embodiments, the water-soluble adhesive layer comprises a water-soluble acrylic polymer (e.g., but not limited to acrylic acid polymer or acrylic acid ester/acrylic acid copolymer). In some embodiments, the water-soluble adhesive comprises a pressure-sensitive polymeric adhesive. In some embodiments, the adhesive layer does not comprise a rubber adhesive.

The water-soluble adhesive layer is attached to a solid substrate, e.g., a solid support. The solid support typically allows the tape to be pliable and flexible, e.g., a tape that is easily bent or shaped. The thickness of the tape can be varied provided that the tape remains pliable. In some embodiments, the solid substrate is a water-soluble solid substrate, e.g., a water-soluble solid substrate that is dissolvable in a similar condition as that of a water-soluble adhesive described above. In some embodiments, the water-soluble solid substrate comprises cellulose. An exemplary water-soluble solid substrate is a wood-fiber based solid substrate.

Any size and/or shape of adhesive tapes can be used. For example, adhesive tapes can be fabricated into circular discs, squares, or any other shapes. The adhesive tapes can have a surface area of between 0.5 square inches and 4 square inches, or between 1 square inches and 2 square inches. The size and shape of the adhesive tapes can vary depending on the size and/or location of a target site to which the adhesive tapes are applied.

The number of adhesive tapes in each set can vary depending on a number of factors, e.g., the skin condition, the size and/or adhesiveness of the adhesive tapes, the abundance of biological materials present at a target skin site, and any combinations thereof. For example, in some embodiments, the first set, the second set, the third set, and any additional set of the adhesive tapes can each independently contain at least 2 tapes or more, including, e.g., at least 2, at least 3, at least 4, at least 5, at least 6, at least 7, at least 8, at least 9, at least 10, or more tapes. In some embodiments, the first set, the second set, the third set, and any additional set of the adhesive tapes can each independently contain 2-10 tapes, 2-8 tapes, 2-7 tapes, 2-6 tapes, 2-5 tapes, 2-4 tapes, 3-6 tapes, 3-5 tapes, or 3-4 tapes. By way of example only, in some embodiments where the adhesive tape has a surface area of 1 square inches, the first set, the second set, the third set, and any additional set of the adhesive tapes can each independently contain 2-5 tapes. For example, in some embodiments, the first set of the adhesive tapes may contain 3 tapes, while the second set and the third set of the adhesive tapes each may contain 4 tapes. In some embodiments, the first set of the adhesive tapes may contain 7 tapes, while the second set of the adhesive tapes may contain 4 days. In some embodiments, the first set of the adhesive tapes may contain 3 tapes, while the second set of the adhesive tapes may contain 8 tapes.

II. Collection of Biological Materials from Skin Sites Using Water-Soluble Adhesive Tapes Biological materials are collected from a target skin site of a subject by contacting the target skin site of the subject with a series of adhesive tapes, i.e., contacting the target skin site with an adhesive tape following removal of a preceding adhesive tape. The target skin site from which the biological materials are collected may be anywhere on the skin of the subject. For example, a target skin site may be on the ankle, arm (e.g., upper arm or forearm), behind the ear, between fingers, back of the neck, upper back or lower back, legs, or waist. In some embodiments, a target skin site is on the forearm. In some embodiments, the target skin site is substantially void of hair.

The target skin site may be a lesional site or a non-lesional site. In some embodiments, the target skin site may comprise a skin lesion, e.g., a wound, a plaque (e.g., flat, raised patch), or a scaly patch, on the skin or injury to the skin. In some embodiments, the target skin site may not comprise a skin lesion.

The target skin site can be of any size and it is understood that a skilled practitioner will be able to determine the skin sampling size, e.g., based on the skin condition and/or abundance of certain biological molecules at the target skin site. In some embodiments, the target skin site may have a surface area of between 0.5 square inches and 4 square inches, or between 1 square inches and 2 square inches.

The adhesives tapes described herein can be applied to any subjects who need biological materials from skin to be analyzed. In some embodiments, the adhesive tapes can be applied to mammals, for example, human subjects, with or without a skin disease or disorder. In some embodiments, the subjects can be human subjects having, suspected of having, or at risk for a skin disease or disorder. For example, the skin disorder can be psoriasis, dermatitis, a skin infection, an allergic reaction, hives, seborrhea, irritant contact dermatitis, allergic contact dermatitis, hidradenitis suppurativa, allergic purpura, pityriasis rosea, Dermatitis herpetiformis, erythema nodosum, erythema multiforme, lupus erythematosus, a bruise, actinic keratoses, keloid, lipoma, a sebaceous cyst, a skin tag, xanthelasma, basal cell carcinoma, squamous cell carcinoma, melanoma, or Kaposi's sarcoma.

In some embodiments, subjects from which the biological materials are collected can be human subjects having, suspected of having, or at risk for an inflammatory skin disease or disorder. Examples of an inflammatory skin disease or disorder include, but are not limited to acne, rosacea, psoriasis, atopic dermatitis (eczema), seborrheic dermatitis, and contact dermatitis, boils, carbuncles, pemphigus, cellulitis, Grover's disease, hidradenitis suppurativa, and lichen planus. In some embodiments, a subject from which the biological materials are collected can be a human subject having, suspected of having, or at risk for atopic dermatitis.

In some embodiments, a subject from which the biological materials are collected can be a human subject having a systemic disease with cutaneous manifestations. An exemplary systemic disease with cutaneous manifestations is systemic lupus erythematosus (SLE).

In some embodiments, a subject from which the biological materials are collected can be a child who is 18 years old or younger, e.g., 6 months-18 years old, inclusive. In some embodiments, the subject may be a child at the age of 1-2 years old.

In some embodiments, a subject from which the biological materials are collected can be an adult who is over the age of 18, such as 19-80 years old, inclusive. In some embodiments, the subject may be 19-70 years old. In some embodiments, the adult subject from which the biological materials are collected may be an elderly who is over the age of 65, such as 66-80 years old.

Generally, multiple adhesives tapes are applied to a target skin site with pressure to collect biological materials. Pressure can be applied for a reasonable period of time, e.g., between 1 second and 5 minutes, typically between 10 seconds and 45 seconds. In some embodiments, adhesive tapes are applied to a target skin site for 15-20 seconds before removal or stripping. It will be understood that the amount of pressure applied to a skin site and the length of time of stripping can be varied to identify ideal pressures and times for a particular application. Generally, pressure is applied by manually pressing down the adhesive tape on the skin, however, objects, such as blunt, flat objects can be used to assist in applying the tape to the skin to collect biological materials from skin. In some embodiments, each adhesive tape in a set can be applied to a target skin site once or more, e.g., 2 times, 3 times, or more. In other words, in some embodiments, a fresh adhesive tape is used in each application at a target skin site, or a target skin site can be stripped twice or more using the same adhesive tape. In some embodiments, each of the adhesive tapes in the first set each is applied to a target skin site only once. In some embodiments, each of the adhesive tapes in the second and/or third sets each can be applied to the same target skin site at least 2 times or more.

Factors such as the flexibility, pliability, and composition of the adhesive tape used, the time the tape is allowed to adhere to the skin before it is removed, the force applied to the tape as it is applied to the skin, the abundance of biological materials being analyzed, the condition of the skin, and patient/patient variability are typically taken into account in deciding on a protocol useful for a particular tape stripping method in order to assure that sufficient biological materials are collected from a target skin site. In some embodiments, the level and duration of the pressure applied to the tape as it is applied to the skin is determined such that no more than mild transient erythema may occur in subjects after tape application and removal. Thus, the tape collection method is considered non-invasive or minimally invasive.

After the adhesive tapes are collected from a target skin site, the adhesive tapes with biological materials adhered thereto are stored under an appropriate condition in which biological materials to be analyzed remain stable. For example, in some embodiments, the collected adhesive tapes are stored at a temperature of 4° C.-10° C. In some embodiments, the collected adhesive tapes are stored in a reagent that maintains the stability and integrity of the biological materials to be analyzed and dissolves the water-soluble adhesive material of the adhesive tapes to release the adhered biological materials. As an example only, in some embodiments where the adhesive tapes are collected for subsequent downstream nucleic acid analysis, such adhesive tapes can be stored in an aqueous buffer solution, e.g., at a neutral pH, e.g., pH 6, pH 7, or pH 8, and the aqueous buffer solution can comprise a buffer agent (e.g., but not limited to Tris or tris(hydroxymethyl)aminomethane), a polyol (e.g., glycerol or derivative thereof, such as thioglycerol), and/or a protein denaturant (e.g., but not limited to guanidinium thiocyanate). An exemplary buffer is an aqueous buffer solution comprising guanidine thiocyanate, Tris (pH 7-8), and 1-thioglycerol.

In some embodiments where the adhesive tapes are collected for cell culturing, the adhesive tapes can be stored in a cell culture medium and/or stored at room temperature.

In some embodiments, the biological materials extracted from the adhesive tapes can be flash frozen and stored at −80° C. for later use. Typically, this can be performed by snap-freezing using liquid nitrogen or dry ice.

III. Methods of Analyzing the Biological Materials Collected from Water-Soluble Adhesive Tapes Biological materials collected from a target skin site may comprise cells and/or cellular components thereof from a target skin site. Cells may comprise living cells and/or dead cells (including fragments thereof). Cells may comprise microbial cells (e.g., but not limited to bacteria, fungus, yeasts, and/or viruses) from the skin surface of the subjects and/or host skin cells (e.g., keratinocytes and other skin cells) of the subject.

Cellular components are materials derived from cells, including, e.g., but not limited to nucleic acids, polypeptides, lipids, carbohydrates, small molecules, and combinations of any of these. Nucleic acids generally include DNA (e.g., genomic DNA) and RNA (including messenger RNA (mRNA)). The nucleic acids can be double-stranded or single-stranded. Polypeptides are polymers of amino acid residues, including, e.g., proteins and peptides. Examples of polypeptides include, but are not limited to growth factors, enzymes, metabolites, cytokines, and peptide-based toxins. Lipids include cholesterol, free fatty acids, cellular lipids (e.g., components of the plasma membrane and other organelles), carbohydrate-linked lipids (glycolipids), post-translation lipidation of proteins (e.g., palmitoylation or farneyslation), sphingolipid signaling molecules, endocannabinodis, ceramides, and bioactive lysophospholipids, and any combinations thereof. Small molecules are small organic molecules, which typically have a molecular weight less than 5 kDa, examples of which include, but are not limited to toxins, chemokines, and/or metabolites produced by microbial cells.

As used herein, the "first set of the biological materials" are obtained by contacting a target skin site of a subject with each of a first set of adhesive tapes described herein, such that the first set of the biological materials is adhered to the first set of the adhesive tapes. The first set of the adhesive tapes is the plurality of water-soluble adhesive tapes (e.g., 2-8, 2-7, 2-6, or 2-5) that is first brought into contact with the target skin site.

The "second set of the biological materials" are obtained by contacting the same target skin site of the subject, after the application and removal of the first set of the adhesive tapes, with each of the second set of adhesive tapes described herein, such that the second set of the biological materials is adhered to the second set of the adhesive tapes. The second set of the adhesive tapes is the plurality of water-soluble adhesive tapes (e.g., 2-8, 2-7, 2-6, or 2-5) that is brought into contact with the target skin site immediately after the first set of adhesive tapes.

The "third set of the biological materials" are obtained by contacting the same target skin site of the subject, after the application and removal of the second set of the adhesive tapes, with each of a third set of adhesive tapes described herein, such that the third set of the biological materials is adhered to the third set of the adhesive tapes. The third set of the adhesive tapes is the plurality of water-soluble adhesive tapes (e.g., 2-8, 2-7, 2-6, or 2-5) that is brought into contact with the target skin site immediately after the second set of adhesive tapes.

Each set of the biological materials comprises a plurality of biological molecules and may contain different compositions (e.g., in types and/or amounts). In some embodiments, the first set and the second (and/or the third set) of the biological materials differ in at least one type of biological material. For example, microbial cells (e.g., but not limited to bacteria, fungus, yeasts, and/or viruses) or cellular components thereof (e.g., nucleic acids, polypeptides, lipids, carbohydrates, small molecules (metabolites)) are present in the first set in a level substantially higher than that in the second set and/or in the third set, which, in some instances, may be free of microbial cells. In another example, keratinocytes or cellular components thereof (e.g., nucleic acids, polypeptides, lipids, carbohydrates, small molecules (metabolites)) are present in the second set and/or in the third set in a level substantially greater than those in the first set, which, in some instances, may be free of such. As used herein, the term "substantially greater" or "substantially higher" refers to an increase of at least 30% or more, including, at least 40%, at least 50%, at least 60%, at least 70%, at least 80%, at least 90%, at least 1.1 fold, at least 1.5-fold, at least 2-fold, at least 3-fold, at least 4-fold, at least 5-fold, or higher. In some embodiments, microbial cells (e.g., but not limited to bacteria, fungus, and/or viruses) or cellular components thereof (e.g., nucleic acids, polypeptides, lipids, carbohydrates, small molecules (metabolites)) are present in the first set in a level higher than that in the second set and/or in the third set by at least 50% or more, including, e.g., at least 60%, at least 80%, at least 90%, or higher. In some embodiments, the second set of the biological materials may be free of microbial cells. In some embodiments, keratinocytes or cellular components thereof (e.g., nucleic acids, polypeptides, lipids, carbohydrates, small molecules (metabolites)) are present in the second set and/or in the third set in a level greater than those in the first set by at least 50% or more, including, e.g., at least 60%, at least 80%, at least 90%, or higher. In some embodiments, while the first set of the biological materials may comprise dead keratinocytes (e.g., keratinocytes without nucleus), the first set of the biological materials is free of living keratinocytes.

In some embodiments, the first set of the biological materials comprises biological materials from stratum corneum of the subjects. The materials from the stratum corneum may include materials from the surface of the stratum corneum and/or within the stratum corneum. The stratum corneum is the outermost layer of the epidermis, and is comprised of dead skin cells. It protects the living cells beneath it by providing a tough barrier between the environment and the lower layers of the skin. The stratum corneum is made up of 10 to 30 thin layers of continually shedding, dead keratinocytes. The stratum corneum is also known as the "horny layer," because its cells are toughened like an animal's horn.

In some embodiments, the first set of the biological materials comprises at least one microbial biological material from stratum corneum of the subjects. The microbial biological materials may be extracted or isolated from the first set of the biological materials. Non-limiting examples of microbial biological materials include microbial cells (e.g., bacteria, fungus, viruses, and yeasts) and cellular components thereof (e.g., polypeptides, nucleic acids, lipids, small molecules, etc.). In some embodiments, microbial cells may be isolated from the first set of biological materials for culturing and propagation, e.g., for drug screening to determine the antibiotics resistance of the microbial cells, and/or to determine effective antibiotics against the microbial cells.

Figure 6A:
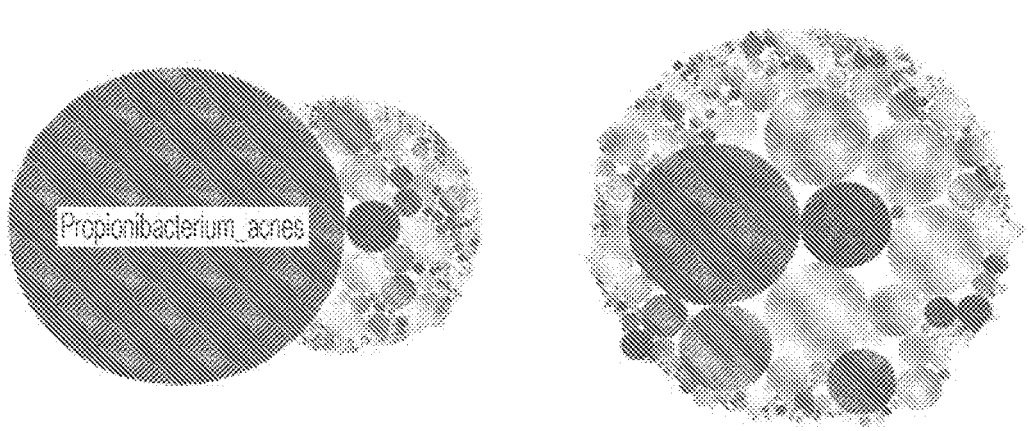
FIGS. 6A-6B are bubble plots showing that tape strip collection as described herein from healthy controls and patients with atopic dermatitis provides quality bacterial DNA for metagenomics shotgun sequencing and analysis.
Figure 6B:
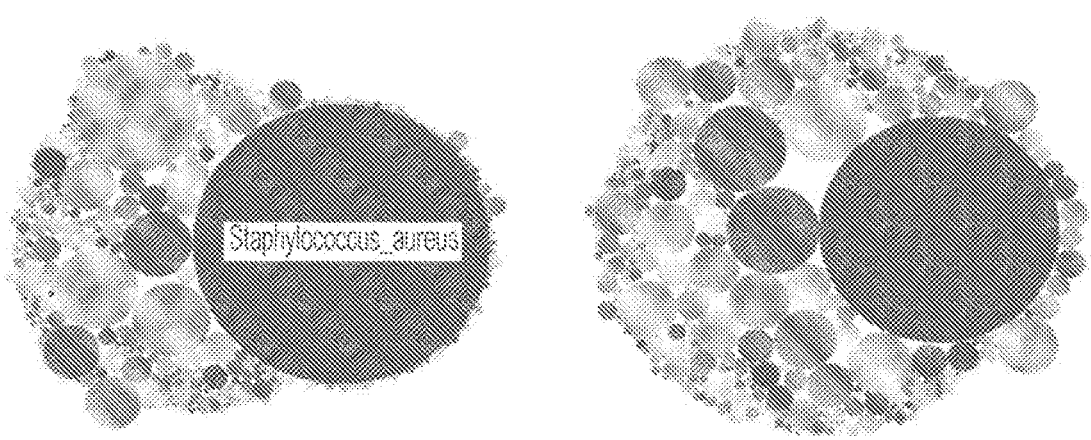
Figure 12:
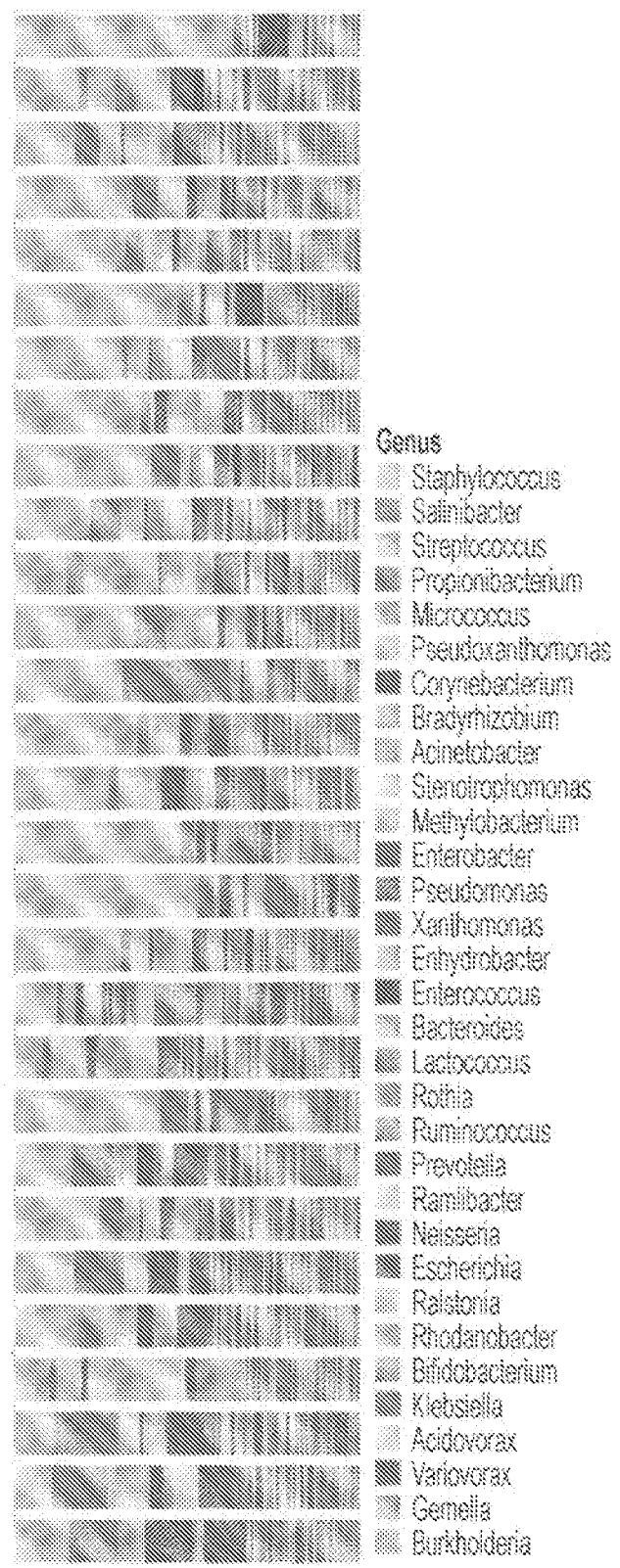
FIG. 12 is a diagram showing metagenomics microbiome data obtained from skin of atopic dermatitis children (e.g., from ages 1-2) using the methods described herein. Microbial DNA from a vast number of bacteria genera were detected using the methods described herein.

In some embodiments, microbial nucleic acids may be extracted from the first set of the biological materials, e.g., for identification of microbial cells. In some embodiments, the microbial nucleic acids may amplified by any methods known in the art, e.g., by polymerase chain reaction, before they are detected and/or analyzed. In some embodiments, microbial DNA may be extracted from the first set of the biological materials and analyzed by shotgun metagenomic sequencing. Shotgun metagenomic sequencing allows comprehensive sampling of all genes in all microorganisms present in a given sample. Thus, microbial species diversity and abundance of microbes can be evaluated based on the microbial nucleic acids extracted from the first set of the biological materials. For example, FIGS. 6A and 6B show that microbial species diversity was detected in the first set of the biological materials collected from healthy controls and subjects with atopic dermatitis. As shown in FIG. 12, a vast number of microbial species can be obtained from skin of atopic dermatitis children (e.g., from ages 1-2) using the methods described herein, which include, e.g., *Staphylococcus, Salinibacter, Streptococcus, Propionibacterium, Micrococcus, Psuedoxanithomonas, Corynebacterium, Bradyrhizobium, Acinetobacter, Stenotrophomonas, Methylobacterium, Enterobacter, Pseudomonas, Xanthomonas, Enhydrobacter, Enterococcus, Bacteroides, Lactococcus, Rothia, Ruminococcus, Prevotella, Ramlibacter, Neisseria, Escherichia, Ralstonia, Rhodanobacter, Bifidobacterium, Klebsiella, Acidovorax, Variovorax, Gemella,* and *Burkholderia*. In some embodiments, microbial nucleic acids may be analyzed by 16S rRNA sequencing.

In some embodiments, the second set, the third set, and/or any additional set of the biological materials comprises host biological materials. Host biological materials are "self" materials of the subject from which the biological materials are obtained. The host biological materials may come from any of the epidermis layers below stratum corneum of the subject from which the biological materials are obtained. For example, the host biological materials may come from stratum lucidum, stratum granulosum, and/or stratum spinosum of the subject. In some embodiments, the host biological materials may comprise keratinocytes and cellular components thereof (including, e.g., nucleic acids, polypeptides, lipids, carbohydrates, and small molecules), for example, from any of the epidermis layers below stratum corneum of the subject from which the biological materials are obtained.

In some embodiments, the presence of the host biological materials may be determined from the second and/or third sets of the biological materials. For example, the presence of biological materials from keratinocytes (including, e.g., cells, nucleic acids, polypeptides, lipids, carbohydrates, and small molecules, etc.) may be analyzed.

In some embodiments, the host biological materials comprise keratinocyte nucleic acids. Methods for analyzing nucleic acids are known in the art. For example, the keratinocyte nucleic acids from the second and/or third sets of the biological materials may be amplified prior to detection and/or analysis. Nucleic acids from the biological materials may be analyzed by any methods known in the art. For example, a nucleic acid may be amplified, prior to analysis by a blotting procedure, e.g., a Northern blot procedure. For blotting procedures polynucleotides are separated on a gel and then probed with a complementary polynucleotide to the sequence of interest. For example, RNA is separated on a gel transferred to nitrocellulose and probed with complementary DNA to one of the genes of interest (e.g., skin biomarkers and/or biomarkers associated with a skin disease or disorder). The complementary probe may be labeled radioactively, chemically etc. In some embodiments, nucleic acids can be detected and/or analyzed by size fractionation. Methods of size fractionating nucleic acids are well known to those of skill in the art, such as by gel electrophoresis, including polyacrylamide gel electrophoresis (PAGE). Size fractionating the nucleic acid may also be accomplished by chromatographic methods known to those of skill in the art. In some embodiments, nucleic acids can be amplified and analyzed for expression of gene(s) of interest (e.g., skin biomarkers and/or biomarkers associated with a skin disease or disorder), e.g., based on RNA or mRNA. To account for variability in amplification reactions, expression level of a target nucleic acid molecule and a control nucleic acid molecule (e.g., a housekeeping gene, such as GAPDH) can be compared to obtain a relative expression level. In some embodiments, nucleic acids (e.g., genomic DNA) of gene(s) of interest (e.g., skin biomarkers and/or biomarkers associated with a skin disease or disorder) can be analyzed by sequencing the nucleic acid. In some embodiments, the nucleic acids can be analyzed by nucleic acid microarrays. In some embodiments, atopic dermatitis-related genes, e.g., S100A8 and KIF3A, or any other signature genes as described in Ghosh et al. "Multiple transcriptome data analysis reveals biologically relevant atopic dermatitis signature genes and pathways" (2015) PloS ONE 10 (12): e0144316, can detected and/or analyzed from the second set and/or third set of the biological materials. In some embodiments, genomic DNA from the second set of the biological materials can be detected or analyzed by sequencing.

In some embodiments, the host biological materials may comprise polypeptide products of one or more genes (e.g., genes encoding polypeptides associated with a skin disease or disorder, e.g., atopic dermatitis). Methods for detecting and analyzing polypeptides are known in the art, e.g., by immunoassay or microarrays. For example, in some embodiments, immunomodulatory molecules involved in atopic dermatitis, including, e.g., but not limited to Th2 mediators interleukin (IL)-4, IL-13, CCL2 (monocyte chemotactic protein-1), CCL22 (macrophage-derived chemokine), and CCL17 [thymus and activation-regulated chemokine (TARC)], IL-1$\beta$, IL-2, IL-8 (CXCL8), IL-10, acute-phase protein serum amyloid A, C-reactive protein, and vascular adhesion molecule-1, CCL17, IL-8 may be detected and/or analyzed from the second and/or third set of the biological materials.

In some embodiments, a different biological material may be extracted from each of the first set, second set, and the third set of the biological materials for different analyses. For example, microbial biological materials (e.g., microbial nucleic acids) can be extracted from the first set of the biological materials for analysis of microbial species diversity and/or abundance of each species. Host biological materials (e.g., epidermal biological materials) may be extracted from the second and/or third sets of the biological materials. For example, host epidermal genomic DNA from the second set of the biological materials can be analyzed for certain gene(s) of interest (e.g., keratinocyte-specific markers and/or skin disease or disorder-associated markers), e.g., for genomic and/or epigenetic assessment. Host epidermal RNA from the third set of the biological materials can be analyzed for expression level of certain gene(s) of interest (e.g., keratinocyte-specific markers and/or skin disease or disorder-associated markers).

In some embodiments, host lipids (i.e., "self" skin lipids of a subject from which the biological materials are obtained) can be extracted from any sets (e.g., the first set, second set, third set, and/or any additional set) of the biological materials collected from the adhesive tapes, for example, where there may be depth difference in where the lipid would come from each subject. The host lipid may come from stratum corneum or an epidermis layer under the stratum corneum. In some embodiments, the second set of the biological materials may be analyzed for host lipids. Examples of host lipids to be analyzed include, but are not limited to cholesterol, free fatty acids, sphingolipid signaling molecules, endocannabinoids, ceramides, and/or bioactive lysophospholipids. Methods for analyzing lipidomics are known in the art. For example, multi-component lipid liquid chromatography-mass spectrometry (LC-MS)/MS analysis and/or high-performance thin-layer chromatography can be performed to analyze a lipid composition of the skin. Such lipid analysis can be used to determine if the lipid content is abnormal and how this relates to a skin condition or disease. In some embodiments, one or more lipids can be used as a diagnostic or prevention biomarker to identify subjects (e.g., children) having, or suspected of having, or at risk for eczema and for eventual development of asthma. In some embodiments, one or more lipids can be used as a treatment biomarker to determine whether a subject is responsive to a treatment, e.g., comprising topical ceramides or other topical agents. In some embodiments, lipid information can be used to determine how dyslipidosis in skin impacts immune responses in keratinocytes.

In some embodiments, the first set of the biological materials comprising microbial biological materials (e.g., ones as described herein such as microbial nucleic acids) is provided by the first set of the adhesive tapes that contains 7 water-soluble adhesive tapes (tapes 1-7, e.g., ones as described herein), while the second set of the biological materials comprising host biological materials (e.g., ones as described herein such as epidermal RNA) is provided by the second set of the adhesive tapes that contains 4 water-soluble adhesive tapes (tapes 8-11, e.g., ones as described herein). In some embodiments, the first set of the biological materials comprising microbial biological materials (e.g., ones as described herein such as microbial nucleic acids) is provided by the first set of the adhesive tapes that contains 3 water-soluble adhesive tapes (tapes 1-3, e.g., ones as described herein), while the second set of the biological materials comprising host biological materials (e.g., ones as described herein such as epidermal DNA and/or RNA) is provided by the second set of the adhesive tapes that contains 8 water-soluble adhesive tapes (tapes 4-11, e.g., ones as described herein). In some embodiments, the first set of the biological materials comprising microbial biological materials (e.g., ones as described herein such as microbial nucleic acids) is provided by the first set of the adhesive tapes that contains 3 water-soluble adhesive tapes (tapes 1-3, e.g., ones as described herein), while the second set of the biological materials comprising host biological materials (e.g., ones as described herein such as epidermal DNA) is provided by the second set of the adhesive tapes that contains 3 water-soluble adhesive tapes (tapes 4-7, e.g., ones as described herein) and the third set of the biological materials comprising host biological materials (e.g., ones as described herein such as epidermal RNA) is provided by the third set of the adhesive tapes that contains 3 water-soluble adhesive tapes (tapes 8-11, e.g., ones as described herein).

The analysis from each set of the biological materials can be combined to determine a biological material profile of a target skin site from which the biological materials are collected. Thus, a skin condition of a subject from which the biological materials are collected can be assessed accordingly. In some embodiments, the skin condition can be assessed before and after a treatment to monitor therapy efficacy and/or to determine appropriate treatment regimen. For example, in some embodiments where a subject has atopic dermatitis, a biological material profile of a skin site (e.g., an affected skin site) of the subject can be determined before and after a treatment to monitor therapy efficacy and/or to determine appropriate treatment regimen. In some embodiments, a subject can be diagnosed for a skin disease or disorder based on the determined biological material profile, as compared to a reference biological material profile (e.g., a biological material profile obtained from subjects without the skin disease or disorder).

IV. Kits for Assessing Skin Condition of Subjects

Another aspect of the present disclosure relates to kits for assessing skin condition of subjects. Accordingly, in some embodiments, such a kit can comprise (a) one or more reagents for extracting biological materials adhered to water-soluble adhesive tapes; and (b) one or more detection agents for determining presence of microbial biological materials and/or host biological materials.

Reagents for extracting biological materials adhered to water-soluble adhesive tapes may include an agent that dissolves the water-soluble adhesive tapes. Such reagents may also comprise an agent that stabilizes at least one of the biological materials to be analyzed. For example, an exemplary reagent is an aqueous buffer solution can comprise a buffer agent (e.g., but not limited to Tris or tris(hydroxymethyl)aminomethane), a polyol (e.g., glycerol or derivative thereof, such as thioglycerol), and/or a protein denaturant (e.g., but not limited to guanidinium thiocyanate). In some embodiments, the reagent may be an aqueous buffer solution comprising guanidine thiocyanate, Tris (pH 7-8), and 1-thioglycerol.

In some embodiments, the kit can further comprise agents for isolating and/or purifying a target biological material from a mixture of biological materials. In some embodiments, the kit can comprise agents for isolating and/or purifying a target microbial biological material and/or host biological material. Such agents can include, but are not limited to agents for isolating and/or purifying microbial nucleic acids (e.g., DNA or RNA), host epidermal DNA, host epidermal RNA, host epidermal lipid, and any combinations thereof. In some embodiments, the kit can comprise (i) agents for isolating and/or purifying microbial nucleic acids (e.g., DNA or RNA), and (ii) agents for isolating and/or purifying epidermal genomic DNA. In some embodiments, the kit can comprise (i) agents for isolating and/or purifying microbial nucleic acids (e.g., DNA or RNA), and (ii) agents for isolating and/or purifying epidermal RNA. In some embodiments, the kit can comprise (i) agents for isolating and/or purifying microbial nucleic acids (e.g., DNA or RNA), and (ii) agents for isolating and/or purifying epidermal lipids. In some embodiments, the kit can comprise (i) agents for isolating and/or purifying microbial nucleic acids (e.g., DNA or RNA), (ii) agents for isolating and/or purifying epidermal genomic DNA, and (iii) agents for isolating and/or purifying epidermal RNA. In some embodiments, the kit can comprise (i) agents for isolating and/or purifying microbial nucleic acids (e.g., DNA or RNA), (ii) agents for isolating and/or purifying epidermal genomic DNA, (iii) agents for isolating and/or purifying epidermal RNA, and (iv) agents for isolating and/or purifying epidermal lipid. Reagents and materials for isolating and/or purifying these biological materials are known in the art and are commercially available. By way of example only, agents for isolating and/or purifying epidermal RNA may include, but are not limited to, lysis buffer, Trizol, chloroform, isopropanol, DNase, clean-up columns, and any combinations thereof.

In some embodiments, the detection agent(s) provided in the kit can comprise a microbial culture medium (e.g., a liquid medium or a solid medium such as agar), an agent for detecting microorganisms, an agent for detecting host biological materials, or a combination thereof. Agents are detecting microorganisms and/or host biological materials can vary depending on the types of biological molecules to be detected. For example, agents for detecting nucleic acids from microorganisms and/or host biological materials may include oligonucleotide primers and probes, e.g., for amplification and detection of gene of interests, and amplification agents, e.g., DNA polymerase. For example, in some embodiments, the oligonucleotide primers and probes may be designed for amplifying and/or detecting housekeeping genes (e.g., but not limited to GAPDH), keratinocyte-specific genes (e.g., but not limited to keratin 1), and/or skin disease-related genes. For example, in some embodiments where the kit is used to assess skin condition of a subject having, suspected of having, or at risk for atopic dermatitis, the kit can comprise oligonucleotide primes and probes for atopic dermatitis-related genes (including, e.g., but not limited to S100A8 and KIF3A).

Agents for detecting polypeptides from microorganisms and/or host biological materials may include capture antibodies against specific protein or peptide to be analyzed, detection antibody (e.g., a labelled antibody), a blocking agent (e.g., bovine serum albumin), and any combinations thereof. For example, in some embodiments where the kit is used to assess skin condition of a subject having, suspected of having, or at risk for atopic dermatitis, the kit can comprise capture antibodies for atopic dermatitis-related proteins or peptides (including, e.g., but not limited to immunomodulatory molecules associated with atopic dermatitis such as those as described herein).

In some embodiments, the detection agents provided in the kit can comprise (i) an agent for preparing a microbial DNA library, e.g., for metagenomic shotgun sequencing, or for 16S rRNA sequencing; and (ii) an agent for detecting the presence of epidermal DNA (e.g., sodium bisulfite for bisulfite pyrosequencing). In some embodiments, the detection agents can comprise (i) an agent for preparing a microbial DNA library, e.g., for metagenomic shotgun sequencing, or for 16S rRNA sequencing; and (ii) an agent for detecting the presence of epidermal RNA (e.g., agents for performing reverse transcriptase reaction and oligonucleotide primers and probes for amplifying and/or detecting expression of gene(s) of interest). In some embodiments, the detection agents can comprise (i) an agent for preparing a microbial DNA library, e.g., for metagenomic shotgun sequencing, or for 16S rRNA sequencing; and (ii) an agent for detecting the presence of epidermal lipid. In some embodiments, the detection agents provided in the kit can comprise (i) an agent for preparing a microbial DNA library, e.g., for metagenomic shotgun sequencing, or for 16S rRNA sequencing; (ii) an agent for detecting the presence of epidermal DNA (e.g., sodium bisulfite for bisulfite pyrosequencing); and (iii) an agent for detecting the presence of epidermal RNA (e.g., agents for performing reverse transcriptase reaction and oligonucleotide primers and probes for amplifying and/or detecting expression of gene(s) of interest). In some embodiments, the detection agents provided in the kit can comprise (i) an agent for preparing a microbial DNA library, e.g., for metagenomic shotgun sequencing, or for 16S rRNA sequencing; (ii) an agent for detecting the presence of epidermal DNA (e.g., sodium bisulfite for bisulfite pyrosequencing); (iii) an agent for detecting the presence of epidermal RNA (e.g., agents for performing reverse transcriptase reaction and oligonucleotide primers and probes for amplifying and/or detecting expression of gene(s) of interest); and (iv) agents for detecting the presence of epidermal lipid. Reagents and materials for detecting these biological materials are known in the art and are commercially available.

In some embodiments, the kit can further comprise a plurality (e.g., at least 5, at least 10, at least 20, at least 30, at least 40, or more) of water-soluble adhesive tapes such as those described herein. Water-soluble adhesive tapes are adhesive tapes described herein comprising a water-soluble adhesive attached to a substrate. In some embodiments, the water-soluble adhesive tapes can be individually packaged. In some embodiments, the plurality of adhesive tapes can be packaged into multiple subsets, wherein each subset may contain 2-5 adhesive tapes. In some embodiments, the plurality of water-soluble adhesive tapes may be packaged into a roll.

In some embodiments, the kit can further comprise instructions for use in accordance with any of the methods described herein. The instructions can comprise a description of methods of collection of biological materials using water-soluble adhesive tapes, and/or methods of analyzing biological materials collected from the water-soluble adhesive tapes.

Instructions supplied in the kits described herein are typically written instructions on a package insert (e.g., a paper sheet included in the kit), but machine-readable instructions (e.g., instructions carried on a magnetic or optical storage disk) are also acceptable. In some embodiments, the label or package insert may indicates that the kit is used for obtaining a skin biological material profile for subjects having, suspected of having, or at risk for a specific skin disease or disorder, e.g., atopic dermatitis. In some embodiments, the kit may further comprise a reference biological material profile, e.g., a reference skin biological material profile for subjects without a skin disease or condition, e.g., atopic dermatitis, for comparison. In some embodiments, the label or package insert may indicate that the kit is suitable for use in specific groups of subjects, e.g., as described herein. Instructions may be provided for practicing any of the methods described herein.

In some embodiments, the kit may further comprise an application tool for applying adhesive tapes to, and removing adhesive tapes from, a target skin site. Such an application tool may be a tweezer.

Kits may optionally provide additional components such as buffers and interpretive information. Normally, the kit comprises a container and a label or package insert(s) on or associated with the container.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Development of a Non-Invasive Method of RNA Collection from Skin

The understanding of atopic dermatitis (AD) is limited by lack of reliable, noninvasive methods for collection of samples from skin. Tape harvesting method is a noninvasive procedure performed as a way to extract biological samples (including, e.g., DNA and RNA) form the outer layers of the skin, but it is not used to study AD.

Stratum corneum is the most outer layer of the epidermis and provides protection to the underlying tissues against infection, dehydration, chemical and mechanical stress. However, it consists of dead flattened non-nucleated cells filled with keratin (and little to no RNA). Sampling for RNA requires collection of skin below the stratum corneum. Several variables can influence sample collection. This includes, e.g., but not limited to the presence of RNases in the environment that are difficult to eliminate, size and number of sequential tape strips (proxy for depth into the epidermis), and isolation technique. Therefore, there is a need to develop a non-invasive tape-stripping method for RNA collection from skin such that RNA of sufficient quantities and purity can be obtained for use in downstream applications.

Exemplary Methods

FIG. 1 is a diagram showing an exemplary scheme of a non-invasive method of determining a biological material profile of a target skin site.

Collection

To collect biological materials for analyses, eleven 1 sq. in. water-soluble adhesive strips (SmartSolve®, Bowling Green, OH) were applied to a test subject sequentially at the same target skin site (e.g., on anterior forearm). Strips 1-7 were banked for microbiome and DNA isolation, while strips 8-11 for used for RNA isolation.

In some embodiments, biological materials can be collected from a lesional and/or non-lesional skin site.

RNA Isolation

Tapes were added to 4 mL of Trizol reagent and flash frozen/thawed. Disintegrated tape was sedimented by centrifugation. 600 uL of chloroform was added and RNA extraction was performed. Isopropanol precipitation was then performed and pellet was washed with ethanol. Sample was then transferred to Qiagen MinElute cleanup column, followed by DNAse I digestion (Qiagen) performed on column.

Quality Control

Sample yield (concentration and quality) was verified by Nanodrop (Thermo Fisher) and Bioanalyzer (Agilent). Samples were reverse-transcribed using Superscript IV (Invitrogen). qPCR was performed using Roche LightCycler 96 using SYBRGreen with a Touchdown protocol. Genes expression of skin biomarkers and/or skin disease-associated biomarkers (e.g., GAPDH, Keratin1 and S100AB) were measured. RT-non template and a positive control (RNA form HBEC cell line) were utilized for quality control for each gene. SYBRGreen melt-curve and agarose gel electrophoresis were utilized to verify amplification products. In some embodiments, Taqman primer/probe can be used to improve sensitivity and specificity.

In some embodiments, expression analysis of genes of interest can be performed at different levels of tape strips (e.g., strip 8 vs 11) vs single cell vs pooled sample from same individual.

Results

Figure 2:
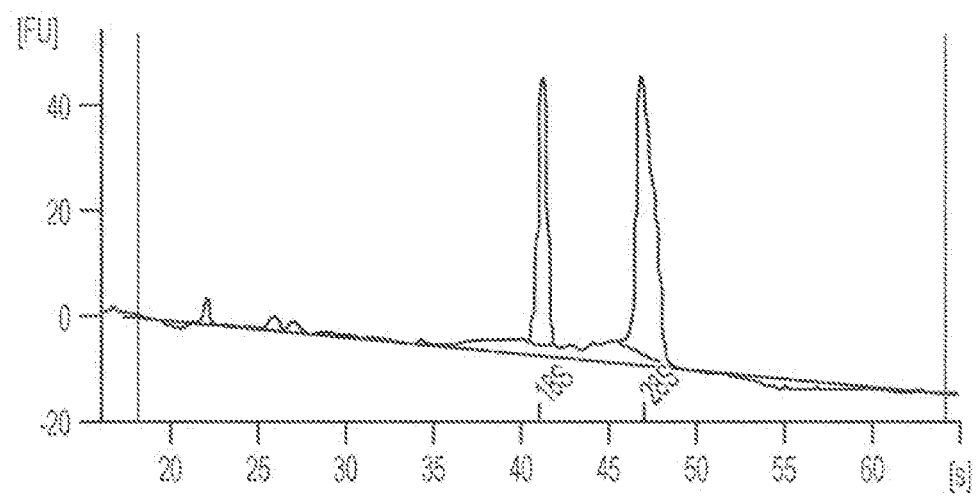
FIG. 2 shows electropherograms of two representative samples (Sample A and Sample B) of RNA collected and isolated according to the process as shown in FIG. 1. The electropherograms show strong 18 s and 28 s peaks (Bioanalyzer). Computer generated RNA agarose gel electrophoresis show strong bands and no degradation.
Figure 2:
Figure 2:
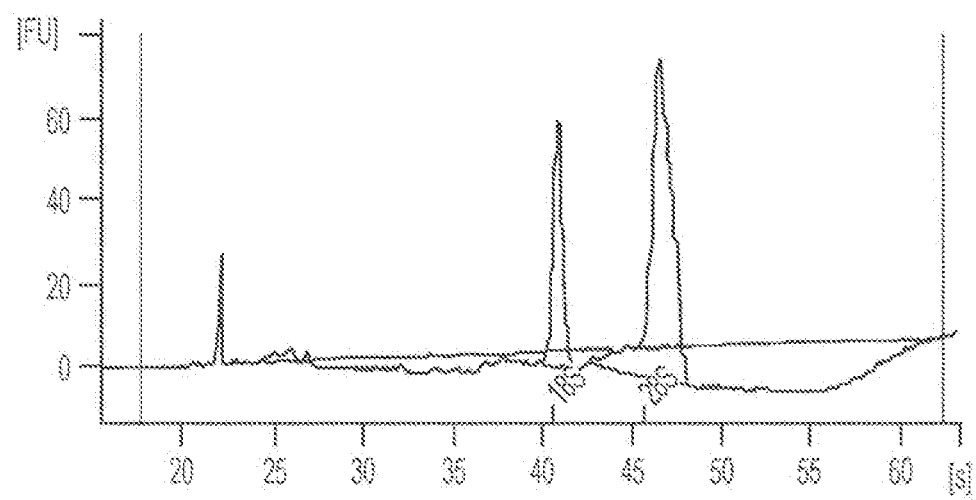
Figure 2:

FIG. 2 shows electropherograms of two representative samples (Sample A and Sample B) of RNA collected and isolated according to the process as shown in FIG. 1. The electropherograms show strong 18 s and 28 s peaks (Bioanalyzer). Computer generated RNA agarose gel electrophoresis show strong bands and no degradation (see FIG. 2).

Figure 3:
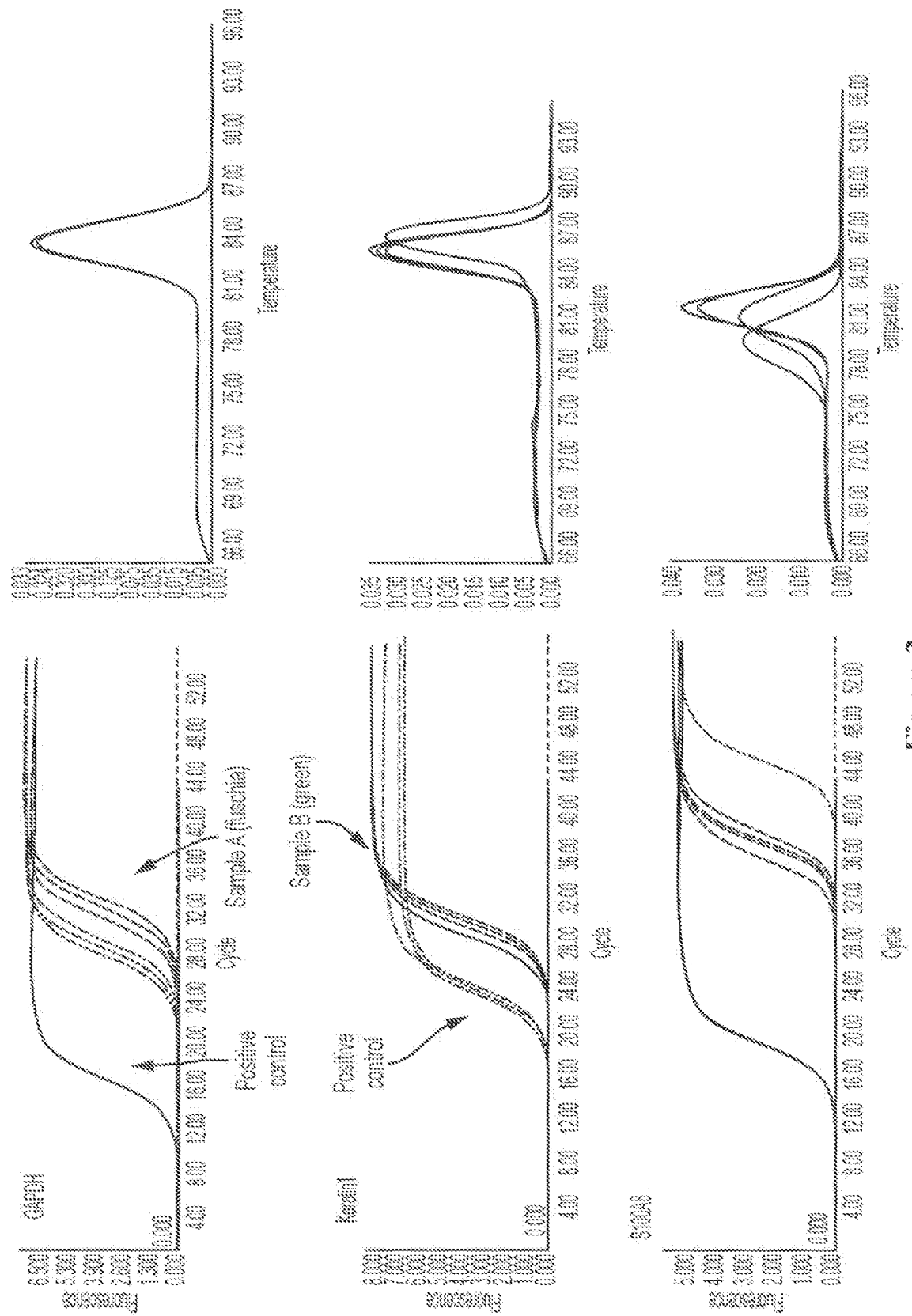
FIG. 3 shows quantitative PCR amplification plots of two representative samples (Sample A; Sample B) in comparison to that of the positive control (HBEC cells) for expression of GAPDH, Keratin1, and S100A8 (left panels). SYBRgreen melt-curves of PCR product from Sample A, Sample B and positive control show superimposed single curves (right panels).

FIG. 3 (left panels) shows quantitative PCR amplification plots of two representative samples (Sample A; Sample B) in comparison to that of the positive control (HBEC) for expression of GAPDH, Keratin1, and S100A8. FIG. 3 (right panels) show that SYBRgreen melt-curves of PCR product from Sample A, Sample B and positive control show superimposed single curves.

Figure 4:
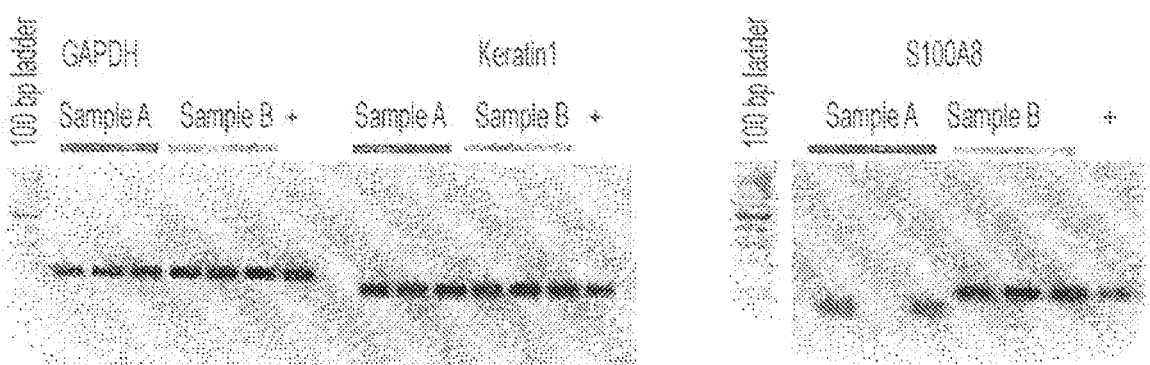
FIG. 4 contains pictures showing agarose gel electrophoresis of qPCR product. Samples run in triplicate with a positive (+) control. Expected amplicon sizes: GAPDH (184 bp), Keratin1 (128 bp), S100A8 (104 bp). Clear bands similar to the positive control are present in GAPDH, Keratin1, and S100A8 samples. Sample 1 in S100A8 had poor amplification with likely primer dimerization.

FIG. 4 contains pictures showing agarose gel electrophoresis of qPCR product. Samples run in triplicate with a positive (+) control. Expected amplicon sizes: GAPDH (184 bp), Keratin1 (128 bp), S100A8 (104 bp). Clear bands similar to the positive control are present in GAPDH, Keratin1, and S100A8 samples. Sample 1 in S100A8 had poor amplification with likely primer dimerization.

The results show that tape stripping method was well tolerated in test subjects. The only reaction noted was mild transient erythema at the site of the skin taping immediately after the procedure. Increasing the size of a tape strip (e.g., a larger tape strip of 1 sq. in.) resulted in improved DNA/RNA yield and consistency as compared to a smaller tape strip of ½ sq. in. Nanodrop data shows that the RNA samples measured at a 260/280 ratio had a value between 1.6-1.9. No substantial increase in RNA yield was seen in more than $11^{th}$ tape strip. In some embodiments, a single column-based isolation alone can result in clogging of the column. Thus, in these embodiments, multiple step isolation can be applied.

CONCLUSIONS

Tape stripping method is a non-invasive and well tolerated method for collection of biological materials from skin. Tape strip collection results in sufficient RNA yield for use in quantitative RT-PCR. For example, amplification of even low RNA quantities is possible.

Example 2: Rapid Reliable Method for Collection of Keratinocyte RNA and DNA Samples from Children Atopic dermatitis is a common manifestation of atopy, but human-based studies are limited by the lack of reliable, non-invasive methods for collection of biologic samples from skin that can be used for genetic, genomic, and mechanistic studies. This gap in understanding has hindered the development of novel therapies directed to the skin epithelium. Accordingly, there is a need to develop a non-invasive, reliable, and sensitive method of collection of RNA from lesional and non-lesional skin of children with atopic dermatitis. The inventors have developed a tape-based method for non-invasive sampling of skin from children that reliably yields RNA and DNA from keratinocytes with high-quality for development of genomic, epigenetic, and microbiome biomarkers and therapies directed to the skin. This approach can be broadly utilized to study and sample the skin of children and identify and track new disease biomarkers and enable new therapeutic development. This tape method is also applicable to the collection of bacteria, protein, and metabolites.

Method

Water-soluble tapes were utilized to collect samples from non-lesional skin using sequential adhering and removal of strips from the same target skin site of a subject. For example, strips 1-3 are saved for microbiome and genomic analysis, and strips 4-11 for host RNA/DNA analysis. Method parameters include, e.g., (I) tape and adhesive type, (2) size of tape, (3) number of sequential tape samples (proxy for penetration into dermis) and (4) purification technique. RNA/DNA Yield (quantity and quality) was estimated using Nanodrop and bioanalyzer. Usability was gauged through RT-qPCR to quantify expression of housekeeping gene (e.g., GAPDH), keratinocyte-specific markers (e.g., Keratin1), and atopy related genes (e.g., S100A8, and KIF3A). Noninvasiveness of the skin sampling was assessed by appearance of skin rash or discomfort of the test subject.

Results

The tape stripping methods were well tolerated. Water-soluble tapes produced higher RNA/DNA yield and consistent results than water-insoluble tapes (e.g., Tegaderm®). Larger tape resulted in improved yield but less consistent results in some instances. Additional sequential tape samples improved yield and consistency. Purification through Trizol with a precipitation step followed by a column-based cleanup improved consistency, as compared to use of Trizol or column-based protocol alone. RT-qPCR showed a high level expression of GAPDH, an intermediate level of S100A8 and Kertain1, and a low level expression of KIF3A.

These results show that a tape-based method can be used for non-invasive sampling of skin from children with atopic dermatitis. This method reliably yields RNA that is of high-quality and enables genomic and epigenetic studies, and can be broadly applied to adults and children, e.g., with skin disorders. Further, the methods described herein can be used to simultaneously collect microbial analytes, e.g., bacteria, protein, and metabolites, from a skin surface, and host analytes (e.g., proteins, DNA, RNA, and metabolites) from an epidermal layer below the skin surface.

Example 3: a Minimally-Invasive Method for Simultaneous Assessment of Epidermal and Microbiome Nucleic Acid Study of dermatologic diseases lack rapid and reliable minimally-invasive tools by which to collect skin samples for biomarker identification as well as for mechanistic, epigenetic, and genomic studies. Skin biopsies require highly-trained healthcare providers, and are invasive, time-consuming, and impractical for collection in large cohorts. Accordingly, there is a need to develop a cost-effective, minimally-invasive, reliable, sensitive, and scalable toolkit and/or method for simultaneous collection of biological materials to assess the skin microbiome and keratinocyte nucleic acids.

Results

General Description of Method and Tolerability

Eleven 1 sq. inch strips of water-soluble adhesive tapes were used to collect epidermal samples from patients using sequential adhering and removal of strips from the same target skin site of each subject. Sequential strips were utilized for simultaneous skin surface microbiome characterization and subjacent keratinocyte epigenetic, genetic studies, and gene expression analyses.

Figure 5:
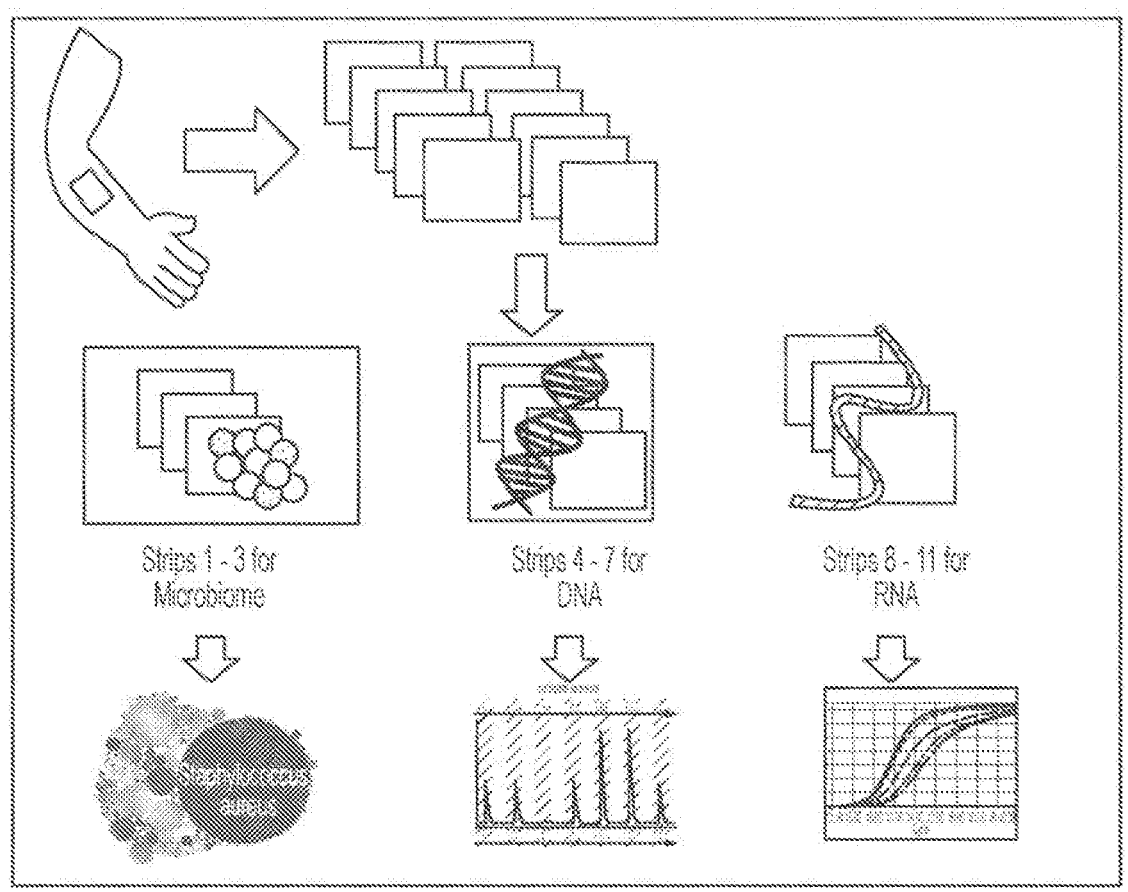
FIG. 5 is a diagram showing an exemplary scheme using tape stripping method to collect biological materials from skin for microbiome, epidermal DNA and epidermal RNA analyses.

The toolkit and/or method utilizes sequentially application and removal of one square inch (1 in×1 in) pieces of water-soluble adhesive tapes (SmartSolve Water Soluble Tape, Bowling Green, OH) (see FIG. 5) to sample the skin. The sterility of the tapes was confirmed using qPCR and culture methods and there was no evidence of microbial contamination. The method was well tolerated from both lesional and non-lesional skin sites in more than 200 children with atopic dermatitis (AD). The only reaction noted was mild transient erythema at the site of the skin taping immediately after the procedure. The first three strips (Strips 1 through 3) were used for isolation of microbial nucleic acid followed by microbiome analysis by metagenomic sequencing. The next three strips (Strips 4 through 7) were utilized for isolation of host epidermal genomic DNA for genomic and epigenomic studies. The last three strips (Strips 8 through 11) were used for isolation of host epidermal RNA for quantification of gene expression.

Figure 10:
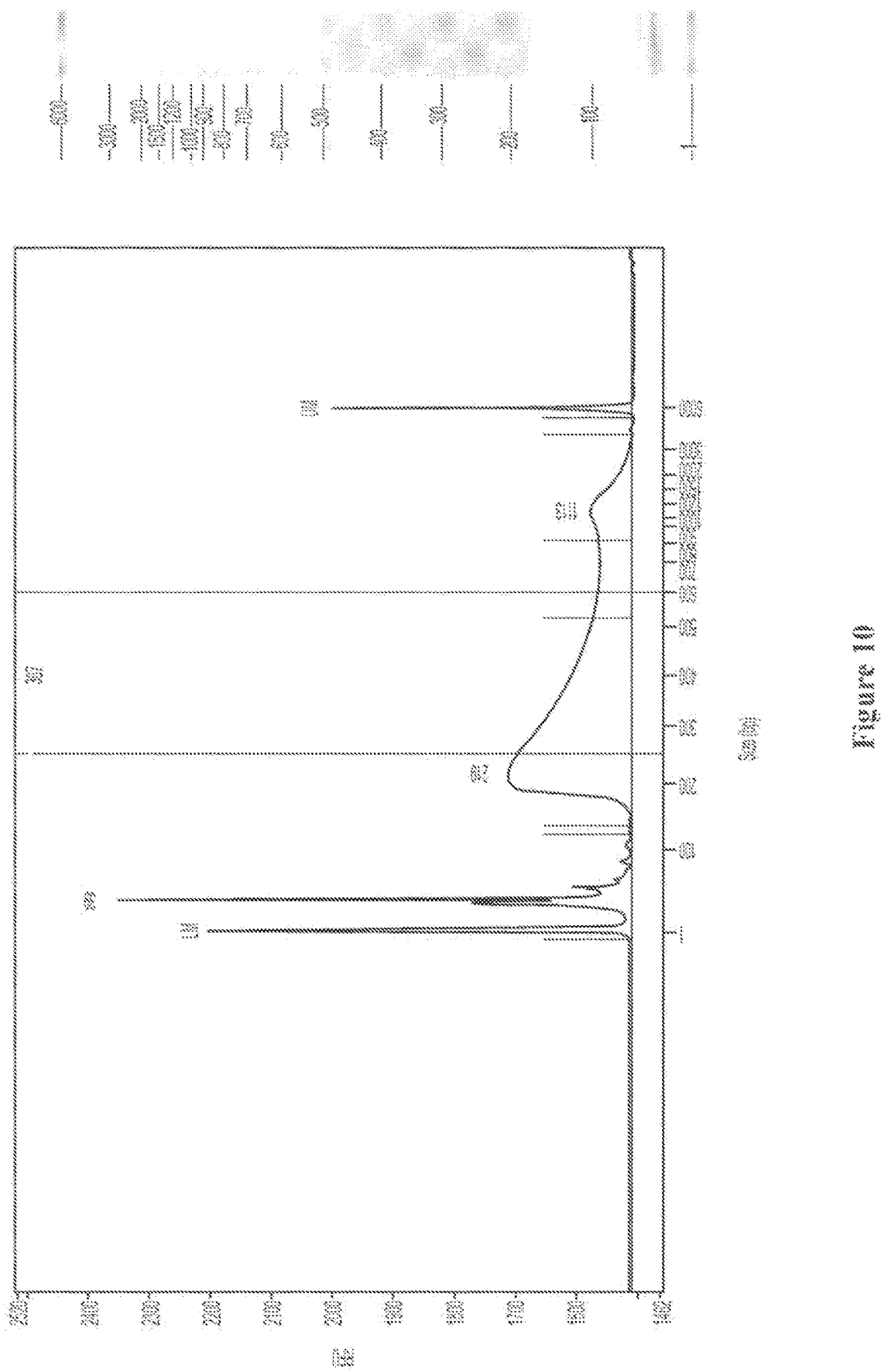
FIG. 10 shows a set of electropherograms of microbiome DNA collected using an exemplary tape stripping method as described herein. The tape strip method provides quality DNA for downstream applications. ATI Bioanalyzer results demonstrate quality DNA fragments between 200 and 600 base pairs.
Figure 10:
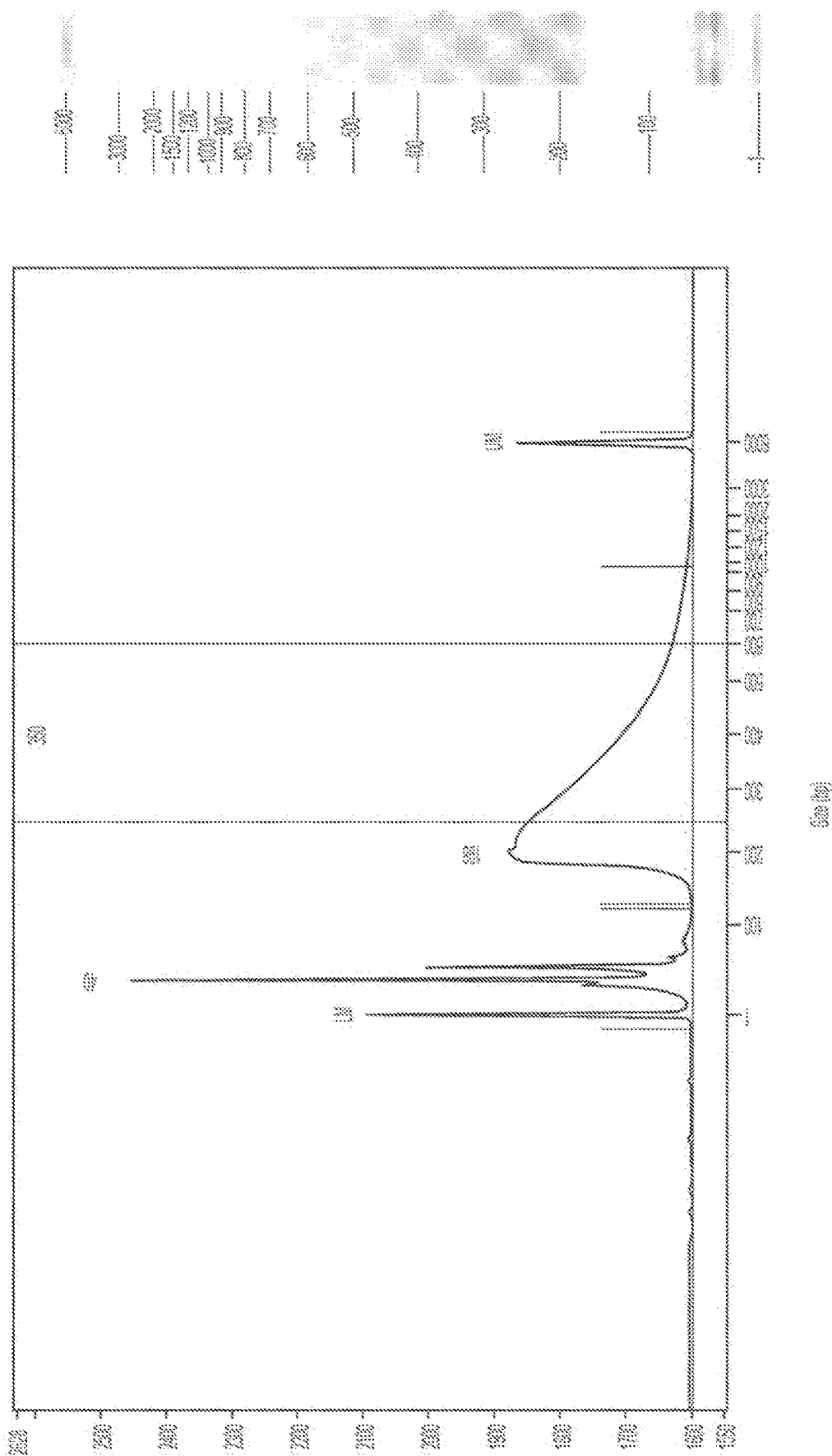
Figure 10:
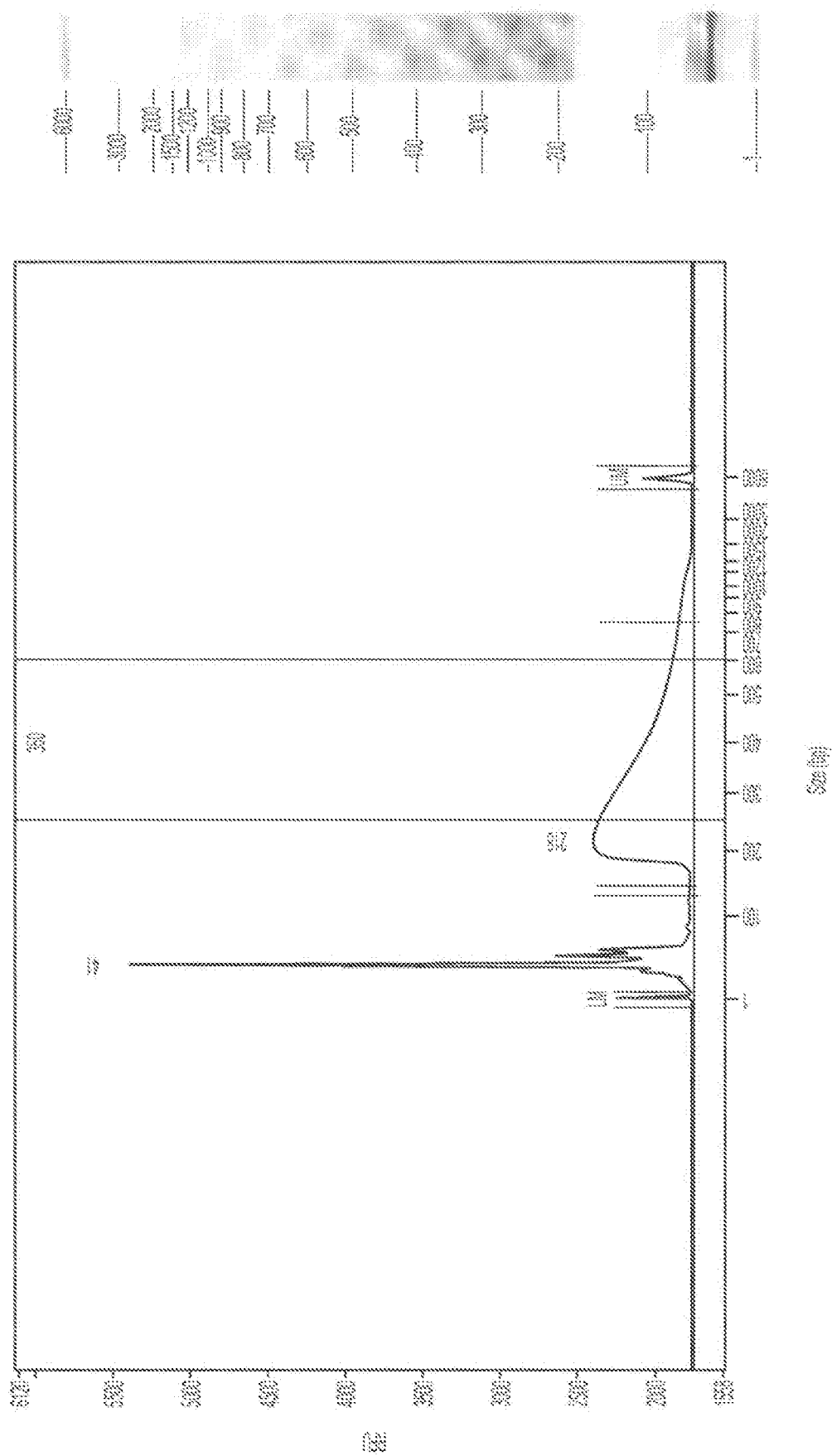
Figure 10:
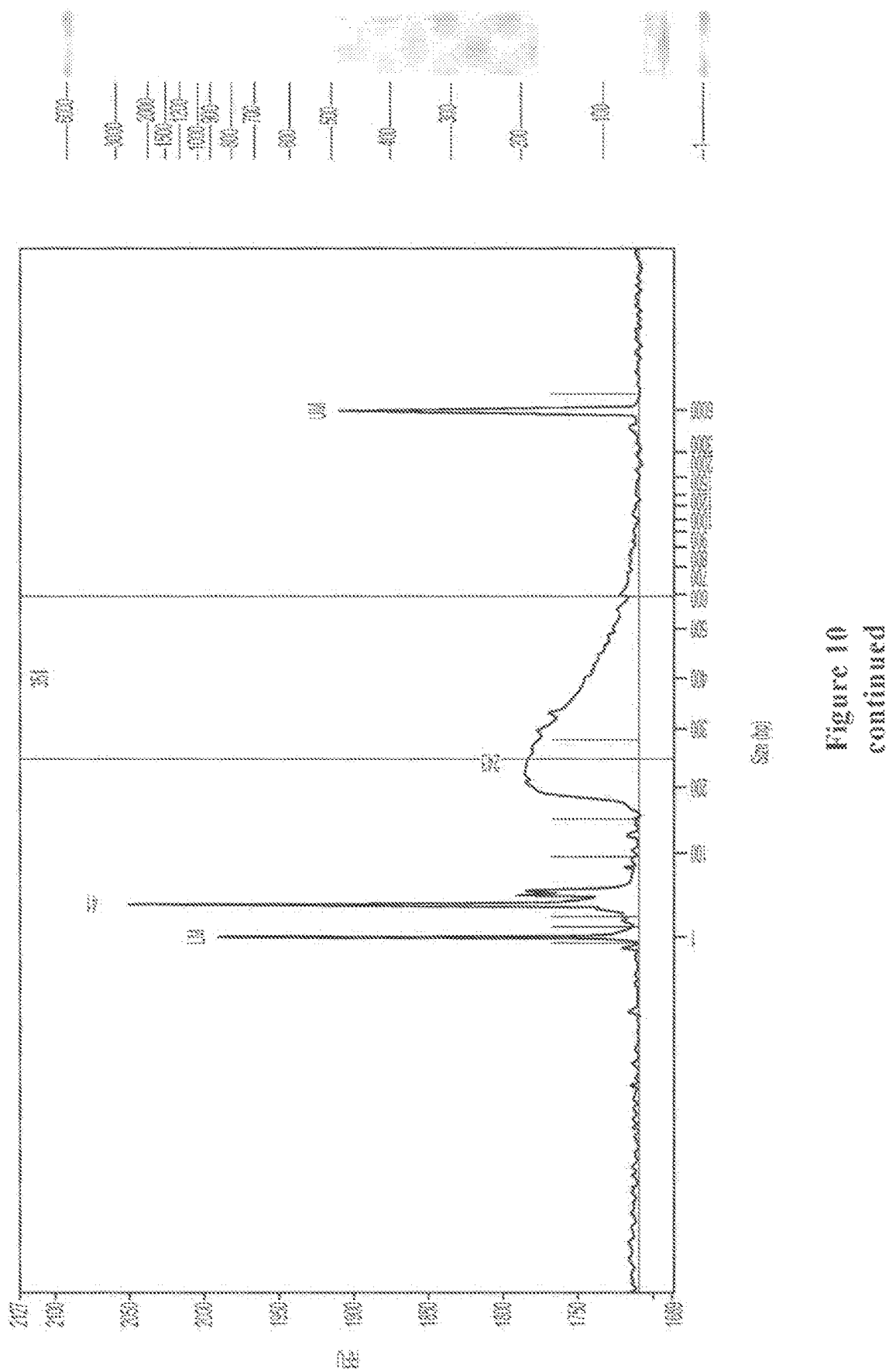

Microbiome Sampling is Effective and Comparable to Contact Agar Plate Collection After microbial DNA purification from the first 3 tapes (see the Methods section below), a bioanalyzer (electropherogram) was used to confirm the integrity of the DNA (see FIG. 10) and then shotgun metagenomics sequencing was performed (see FIGS. 6A-6B).

Use of Epidermal Genomic DNA Isolated from Tapes for Epigenetic Analyses

Figure 7A:
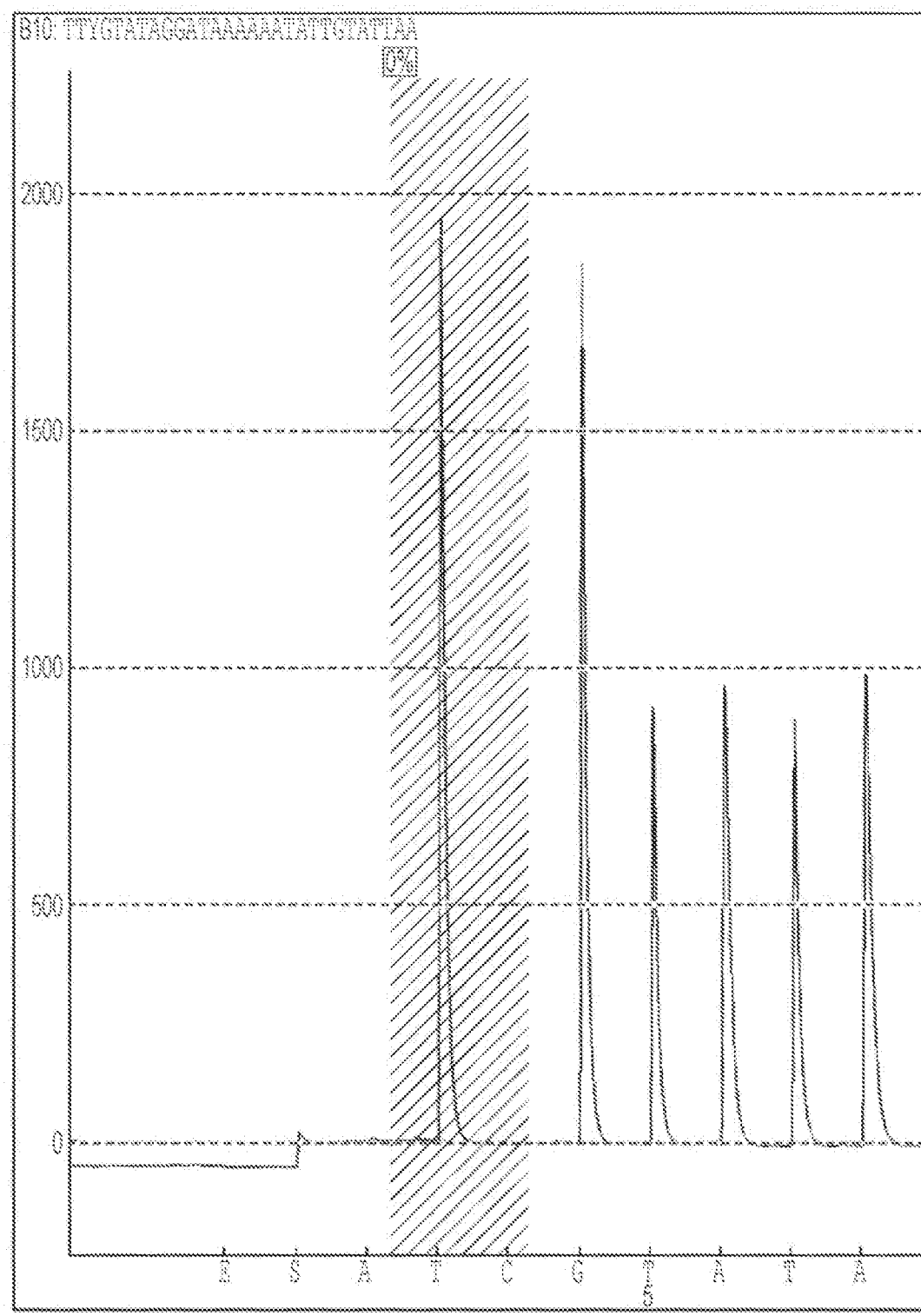
FIGS. 7A-7B are diagrams showing that tape strip collection (e.g., as described herein) from healthy controls provides good quality DNA for downstream pyrosequencing. To access levels of DNA methylation, DNA was extracted from individual tapes, followed by bisulfite treatment and PCR amplification of the region of interest. Two subjects were accessed for their methylation level, one shows 0% methylation (FIG. 7A; SEQ ID NO: 1) while the other 75% methylation (FIG. 7B; SEQ ID NO: 2).
Figure 7B:
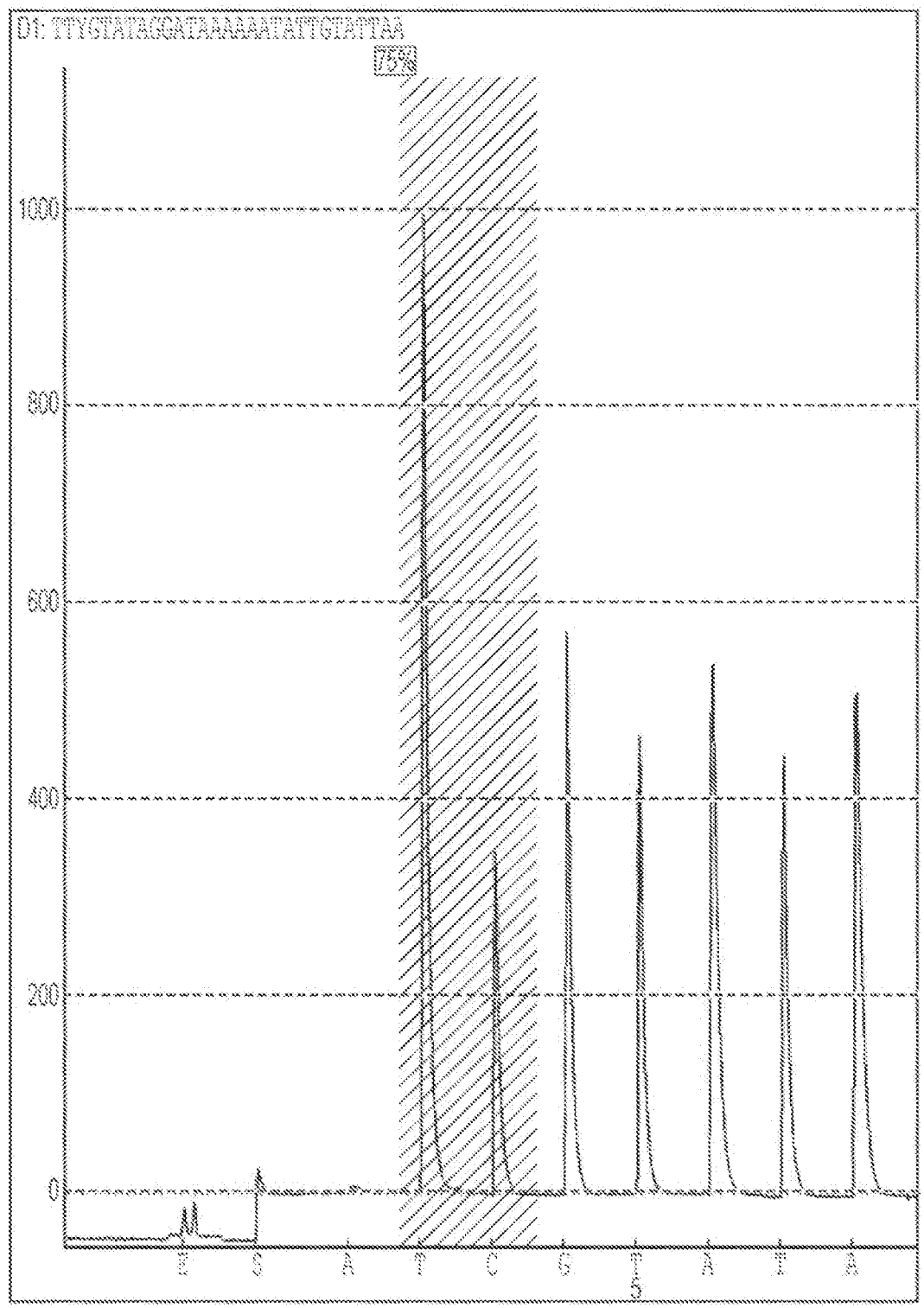

The suitability of the DNA isolated from tape strips four through seven for epigenetic studies was tested by bisulfite pyrosequencing. The DNA was isolated with a column-based commercial kit with a yield ranging from 0.8-1 ng/ul based on Qubit fluorometery. The eluted DNA was bisulfite treated and PCR amplified for a region of interest. The PCR product underwent pyrosequencing and the pyrograms confirmed detection of both unmethylated and methylated DNA (see FIGS. 7A-7B).

Epidermal Sampling Yields Good Quality RNA for qRT-PCR

Figure 8:
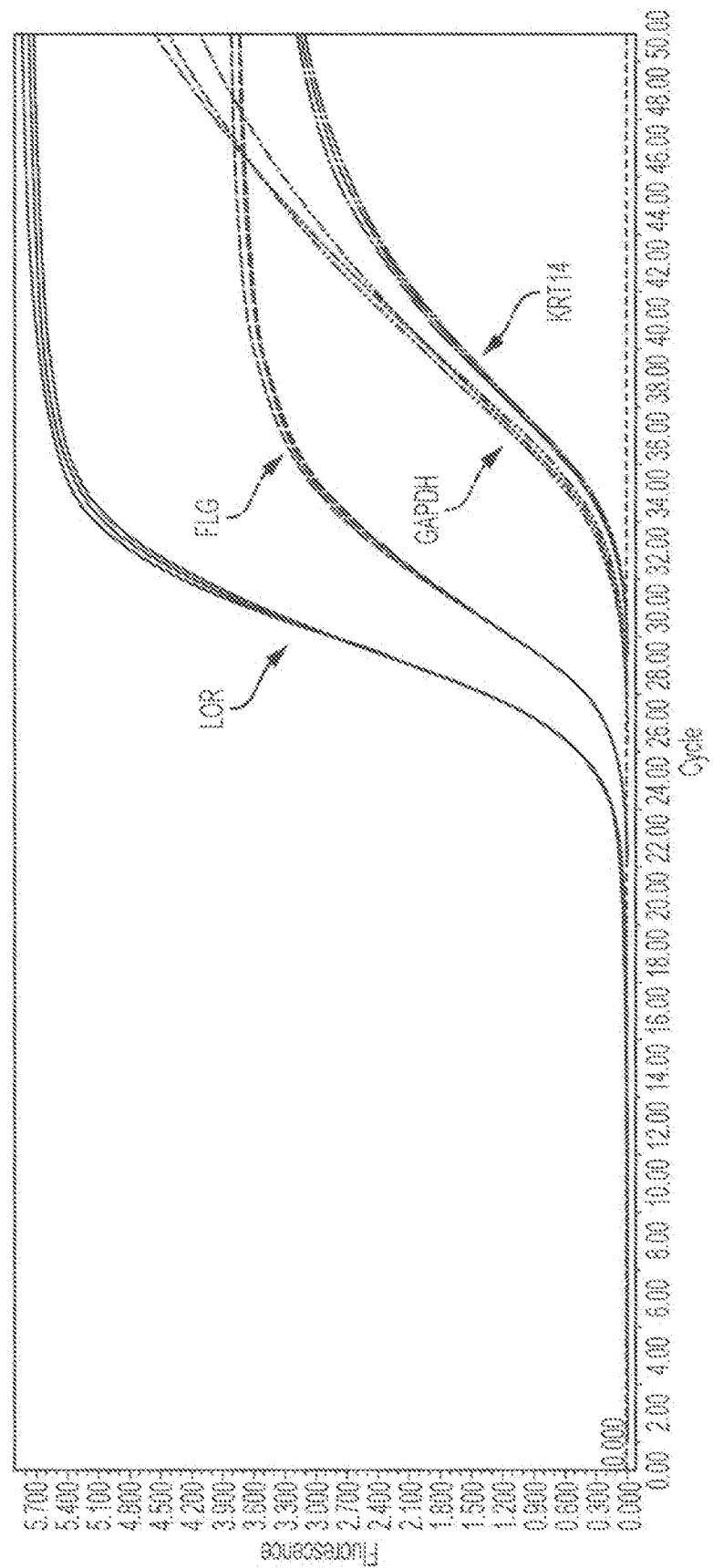
FIG. 8 is an amplification plot showing results of Taqman gene expression assays qRT-PCR. Tape 10 triplicates are shown with each gene: Loricrin (LOR), Filaggrin (FLG), GAPDH, and Keratin 14 (KRT14).
Figure 9:
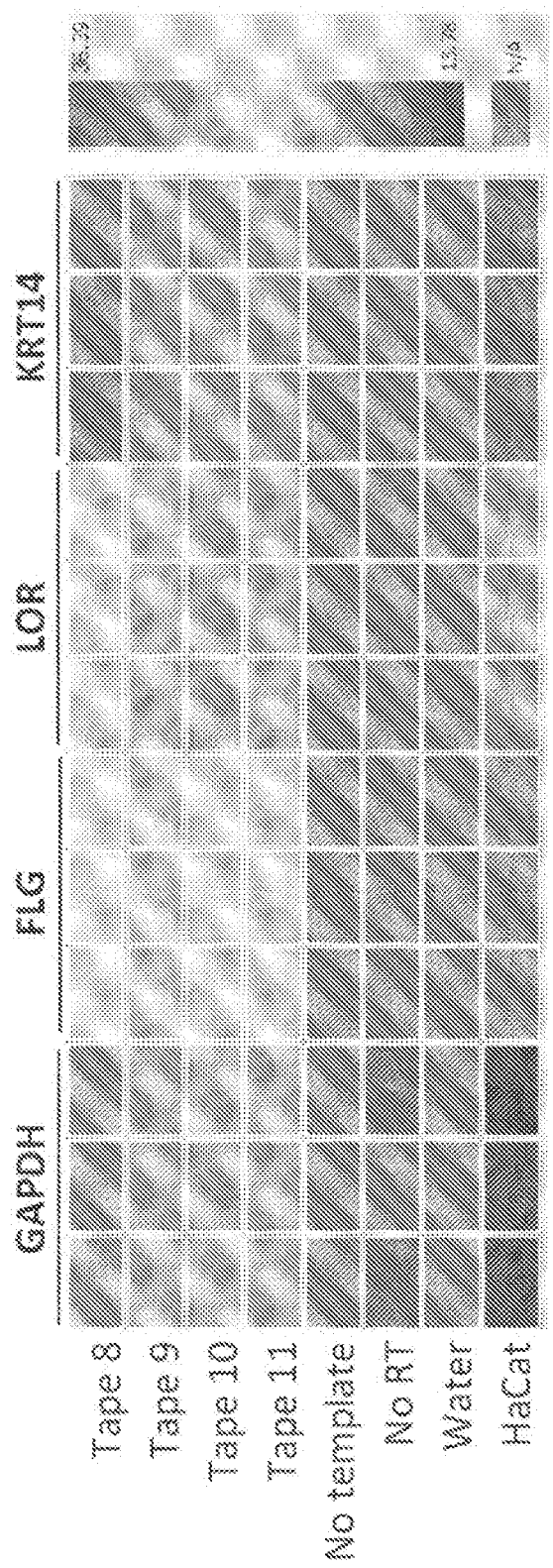
FIG. 9 is a diagram showing that skin sampling from adhesive tapes (e.g., as described herein) provides sufficient RNA for downstream gene expression analysis. Amplification cycle heatmap of tapes 8 through 11 contain high levels of the skin markers FLG, LOR and KRT14. No significant expression was seen in the negative controls (i.e., no template, no RT, and water). HaCat is the human keratinocyte cell line used as a positive control.

Tape strip RNA was isolated with solvent based and column based approaches for better removal of the tape residues. Complementary DNA strand was generated for downstream qRT-PCR to assess skin markers. Several genes were evaluated including Glyceraldehyde 3-phosphate dehydrogenase (GAPDH), Filaggrin (FLG), Loricrin (LOR) and Keratin14 (KRT14), Claudinl (CLDI), Cadherin (CDH), S100A8 and S100A9, ranging from low to high abundance. The success rate of amplification (based on FLG and LOR data) was approximately 90% when samples were run in triplicates. Filaggrin and Loricrin were found to be highly expressed ($C_T$ in mid 30 cycles, FIGS. 8 and 9). Lower expressed genes (such as S100A8 and S100A9 genes) had a lower level of expression ($C_T$ in upper 30 to lower 40 cycles.

Discussion

The described toolkit/method is efficient, low-cost, minimally invasive methodology to collect skin microbial and host epidermal samples {e.g., for keratinocyte nucleic acid isolation) from the same skin site. The samples can be successfully used for skin biome determination, as well as for keratinocyte transcriptomics, genetics, and epigenomics. This technology can be used to explore the molecular underpinnings of skin diseases and to identify targets for therapeutic interventions. The technology can also be used to identify clinically useful biomarkers of skin disease at all different ages and life stages, as well as biomarkers of skin disease severity, barrier dysfunction, physiology, and to aid diagnosis and guide selection of the most optimal treatment. The technology can be readily applied to a wide variety of dermatologic conditions in both research setting and clinical points of care in large cohorts.

The data clearly demonstrates that the toolkit/method described herein yields samples that can be used for metagenomics to delineate the skin biome as well as genetic, transcriptomic, and epigenomic analyses of the underlying keratinocytes. The tapes can also be utilized for lipidomics and metabolomics. The sample collection and processing can use inexpensive off-the-shelf and easily obtainable products, reagents and machinery making the toolkit easy to implement. Further benefits include that it can being easily performed by research or clinic personnel without advanced training, and it is well tolerated by patients without anesthesia. This is a significant advantage when contrasted to the typical collection method of skin biopsy. The methods described herein can easily be modified and scaled to fit the needs of the study/individual. As new techniques and downstream applications emerge, the toolkit can be further adapted to incorporate these new technologies.

In summary, the toolkit/method, specifically the tape sampling method and processing, enabled microbiome analyses that were reliable, reproducible, and approximated the results obtained with traditional contact plate culture methods. The epidermal skin collection yielded keratinocyte DNA and RNA, which were demonstrated to be of sufficient quality and quantity for use in downstream applications such as pyrosequencing, transcriptomics, and real-time PCR.

It is noted that because the source of collection includes cells from the skin surface and/or upper layers of the epidermis (including, e.g., nucleases present on the skin), the integrity of the nucleic acid may be less consistent than that of a sample from biopsies. In order to minimize chemical contamination of the sample, multiple-step purification can be performed to remove the tape substrate and adhesive residue. Multiple tape strips are collected from a single individual and the success rate is collectively close to 100% for qRT-PCR from RNA derived from one of the tape strips. Due to the low quantity of sample, steps should be taken to reduce the risk of contamination, e.g., see the Methods section below.

Use of the Sample Collection Methods Described Herein in Subjects with Atopic Dermatitis The methods described herein were used to explore the molecular signature of atopic dermatitis in the Mechanisms of Progression of Atopic Dermatitis to Asthma in Children (M-PAACH) cohort. In this study, both lesional and non-lesional eczematous skin were sampled from pediatric patients using the toolkit/method described herein to examine the interplay of skin microbiome, epidermal epigenetics and gene expression. More than 4,000 tape strips from over 200 patients were successfully collected.

FIG. 12 is a diagram showing metagenomics microbiome data obtained from skin of atopic dermatitis children (e.g., from ages 1-2) using the methods described herein. Microbial DNA from a vast number of bacteria genera were detected using the methods described herein, examples of which include, but are not limited to *Staphylococcus, Salinibacter, Streptococcus, Propionibacterium, Micrococcus, Psuedoxanithomonas, Corynebacterium, Bradyrhizobium, Acinetobacter, Stenotrophomonas, Methylobacterium, Enterobacter, Pseudomonas, Xanthomonas, Enhydrobacter, Enterococcus, Bacteroides, Lactococcus, Rothia, Ruminococcus, Prevotella, Ramlibacter, Neisseria, Escherichia, Ralstonia, Rhodanobacter, Bifidobacterium, Klebsiella, Acidovorax, Variovorax, Gemella,* and *Burkholderia.*

Figure 13A:
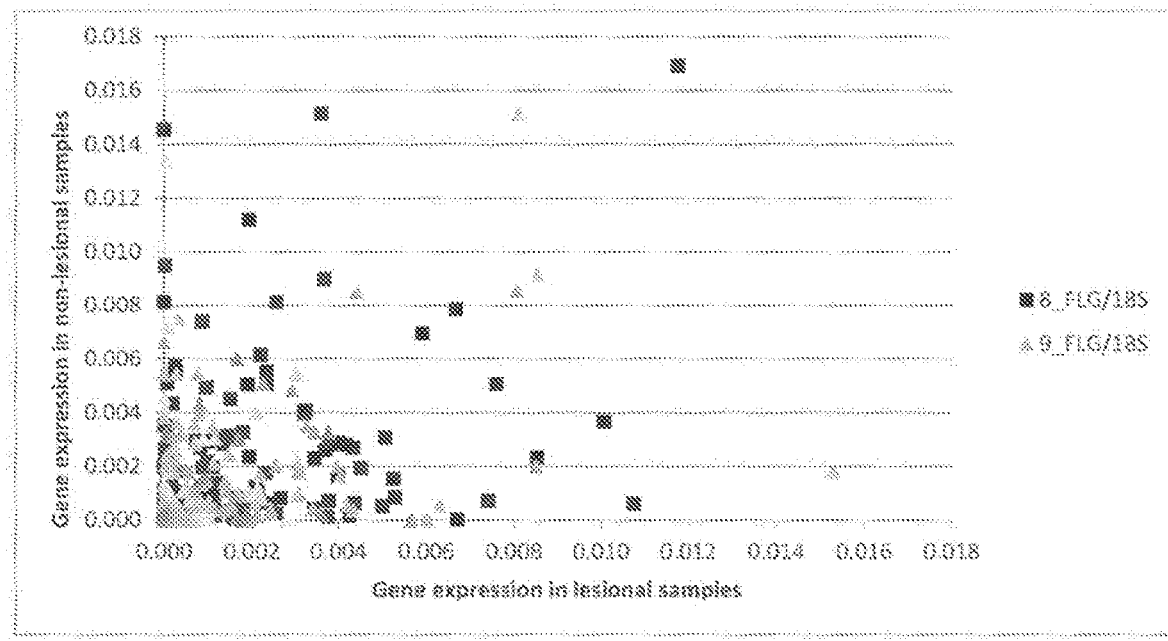
FIGS. 13A-13C are plot graphs showing host RNA/DNA qPCR data corresponding to relative expression levels of filaggrin (FLG) (FIG. 13A), S100A8 (FIG. 13B), and S100A9 (FIG. 13C) at lesional and non-lesional skin sites of about 183 children with atopic dermatitis.
Figure 13B:
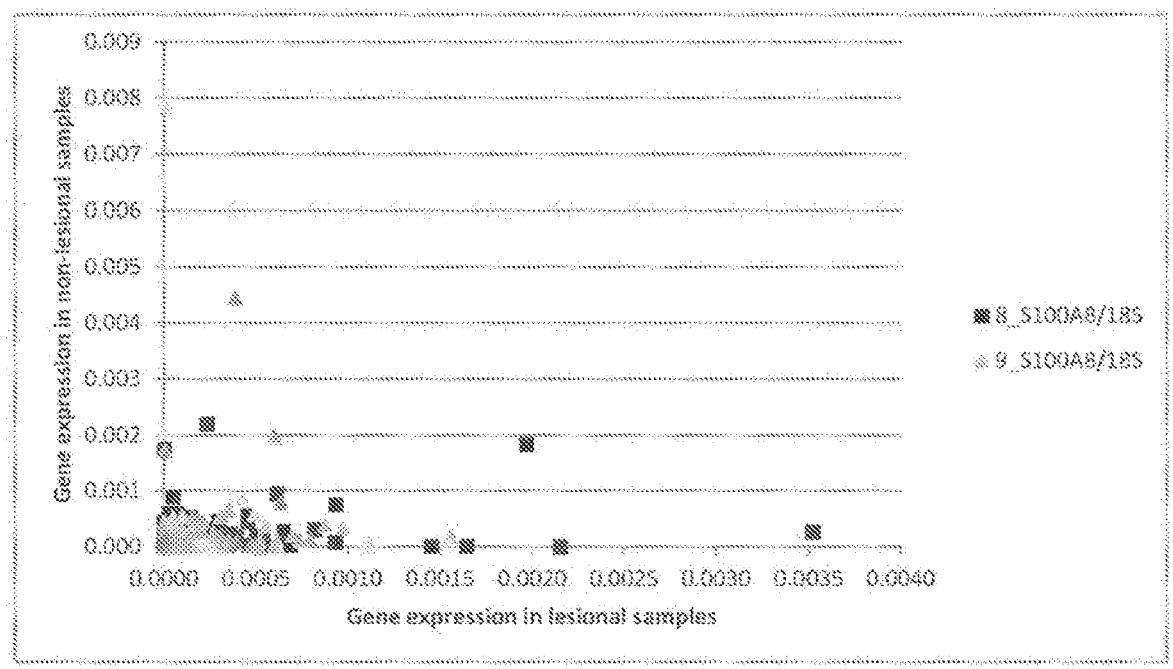
Figure 13C:
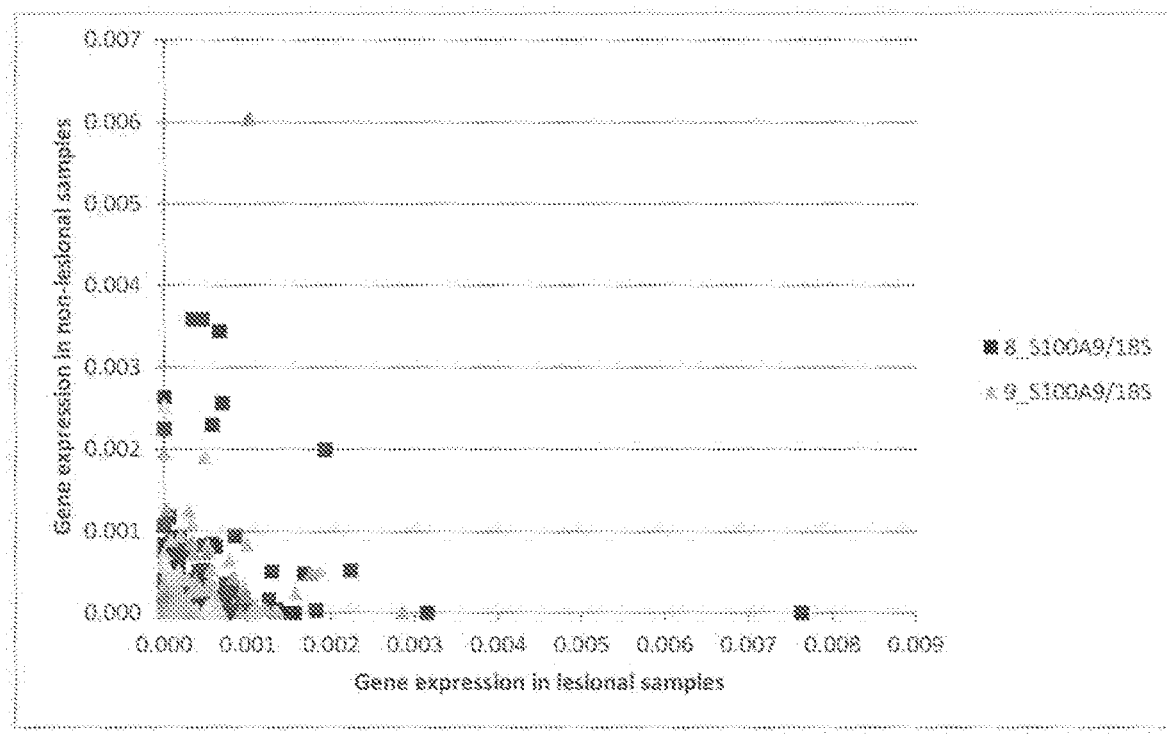

FIGS. 13A-13C are plot graphs showing host RNA/DNA qPCR data corresponding to expression levels of filaggrin (FLG) (FIG. 13A), S100A8 (FIG. 13B), and S100A9 (FIG. 13C) at lesional and non-lesional skin sites of about 183 children with atopic dermatitis.

Exemplary Additional Applications

In addition to atopic dermatitis described above, the methods described herein can be used to explore other markers of other dermatologic diseases or cutaneous manifestation of systemic diseases. In addition, the tapes can be utilized for lipidomics, proteomics, and metabolomics analyses. The methods described herein can be used to better understand the molecular underpinnings of the disease or identify new targets for therapeutic intervention and drug development. The methods described herein can also be used to identify clinically relevant biomarkers of disease—to aid diagnosis, disease severity, predict natural history, or to help select the best treatment strategy. Further, the methods described herein can be utilized at clinical points of care for diagnostic purposes, alone or in concert with biomarkers identified from disease from the skin, blood or other biologic samples. For example, diagnosis of etiology of many rashes generally requires a skin biopsy which could be avoided by making a molecular diagnosis using the methods/kits described herein. The methods/kits described herein can be implemented in a community clinic, doctor's office, urgent care center, or hospital.

In conclusion, presented herein are methods and kits for minimally invasive collection of biological materials from skin, e.g., for use in clinical and research settings for diagnostic and management of skin diseases or even systemic diseases with cutaneous manifestations (such as systemic lupus erythematosus (SLE) and others).

Methods

Collection of Biological Materials From Skin

Keep the buffer and tubes containing the buffer at 4° C.
This ensures the buffer and cells are kept viable for downstream nucleic acid extraction.
1. Wash hands and put on gloves.
2. Identify skin site, preferably void of hair, on the participant. Place the first strip, adhesive side down onto site. Outline site with a highlighter (pen/highlighter maybe used).
If collecting from limb, consider propping participant's limb so that they will be comfortable. The sampling can be lengthy.
Outline site facilitates serial collection from the same location.
3. With gloved hand/finger, gently massage the tape strip on the skin for 15-20 seconds.
Ensures that the strip adheres to as much of the surface area of the site as possible. Massaging of tape should be vigorous, but not painful to participant
4. Remove the tape from the skin with sterilized, duck-billed tweezers.
5. Fold the strip with sterilized tweezers or gloved hand keeping the sticky side to the inside of the tube. Carefully place strips in 1.5 ml tubes and place it on ice. Avoid touching the sticky side with the tweezers.
Tapes 8-11 are taped twice: place the tape strip on the skin, rub it for 15-20 seconds, then turn 90 degrees and re-tape the same region. Massage the skin for another 15-20 seconds, then carefully remove the tape with duck-billed tweezers.
After placement of the tape, invert the tube so the tape can be fully immerged in the buffer.
6. Repeat tape collection at subsequent sites.
7. Transport all tapes on ice.
8. Vortex RNA tapes for 10-25 seconds
Vortexing will help disrupt the tape and improve lysis sooner and will protect against RNAses.
9. Place all tubes on 42° C. heat block or bead-filled water bath for 30 min.
Heat will help denature any proteins collected in the buffer and will help in nucleic acid extraction.
10. After heat block, remove promptly and place in dry ice (5 minutes) or flash frozen in dry ice+ethanol. Posteriorly all tapes are stored in −80° C.

Isolation and Purification of:

Microbial DNA

1. DNA extraction was performed from a single tape strip sample with Promega Wizard Kit®.
2. Vortex the tubes and incubate at 65° C. for 45 minutes to assist in the breakdown of the tape.
3. Centrifuge at 13,000×g for 30 minutes.
4. Transfer the supernatant to a clean tube.
5. Repeat steps 3 and 4.
6. Add 600 ul of Nuclei lysis solution to the supernatant and incubate at 80° C. for 5 minutes.
7. Let the sample cool down to room temperature and add 3 ul of RNase followed by incubation at 37° C. for 30 minutes.
8. Add 200 ul of protein precipitation solution, vortex and place it on ice for 5 minutes.
9. Centrifuge for 3 minutes and transfer the supernatant into a tube containing 600 uL of room temperature isopropanol.
10. Mixed the sample and centrifuge 13000-16000×g for 2 minutes to pellet the DNA.
11. Remove the supernatant and wash the DNA with 600 ul of 70% ethanol.
12. Centrifuge for 13000-16000×g for 2 minutes.
13. Remove the ethanol and air dry the pellet for 10-15 minutes.

14. Resuspend the DNA in 50 uL of DNA rehydration solution and incubate at 65° C. for 1 hour or at 4° C. overnight.
15. Tape residue often remains in the solution, and therefore a final spin of rehydrated DNA is necessary to remove the contaminating pellet. Once centrifuged, the supernatant containing bacterial genomic DNA is removed and stored for downstream applications.

Epidermal Genomic DNA
1. Thaw tubes on ice.
2. Set the thermal block to 70 C.
3. Warm the buffer MBL to 55° C.
4. Transfer individual tapes into bead tubes provided with the QIAmp BiOstic Bacteremia DNA kit.
5. Add 450 µl of Solution MBL to the pellet and resuspend by pipetting.
6. Vortex for 10 seconds to mix and place in a 70° C. heat block for 15 min.
7. Disrupt the tapes with the Bead Ruptor for 1 minute.
8. Centrifuge the PowerBead Tube to pellet debris at 10,000×g for 3 min.
9. Transfer the supernatant to a new 2 ml Collection Tube (provided).
10. Add 100 µl of Solution IRS and vortex to mix.
11. Incubate for 5 min at room temperature.
12. Centrifuge at 10,000×g for 1 min to pellet debris.
13. Transfer the supernatant to a new 2 ml Collection Tube (provided).
14. Add 1 ml of Solution BB. Pipette or pulse vortex to mix.
15. Briefly centrifuge to collect any liquid from the top of the lid.
16. Load 600 µl of lysate onto a MB Spin Column and centrifuge at 10,000×g for 1 min.
17. Discard the flow-through and place the MB Spin Column back into the 2 ml Collection Tube. Repeat this step until all the lysate has been loaded onto the MB Spin Column.
18. Transfer the MB Spin Column to a new 2 ml Collection Tube (provided) and wash by adding 500 µl of Solution CB.
19. Centrifuge 10,000×g for 1 min. Discard the flow-through and put the MB Spin Column back into the 2 ml Collection Tube.
20. Wash with another 500 µl of Solution CB and spin at 10,000×g for 1 min. Discard the flow-through and place the MB Spin Column back into the 2 ml Collection Tube.
21. Centrifuge at 13,000×g for 2 min to dry the MB Spin Column membrane.
22. Transfer the MB Spin Column to a new 2 ml Collection Tube (provided).
23. Elute by adding 50 µl of Solution EB directly in the center of the membrane. Allow the MB Spin Column to sit at room temperature for up to 5 min to maximize the elution.
24. Centrifuge at 10,000×g for 1 min.
25. Discard the MB Spin Column and cap the 2 ml Collection Tube containing the genomic DNA.
26. Centrifuge at 13,000×rpm for 3 minutes and transfer the supernatant to a new tube.
27. DNA can be quantified using intercalating dye kit (such as Qubit). Spectrophotometry has not been shown to be useful.

Epidermal RNA
1. Thaw tubes on ice.
2. Disrupt the tapes with the Bead Ruptor for 30 seconds using *** settings.
3. Centrifuge the tubes at 20,000 rpm (as high as possible) at 4° C. for 30 mins to sediment tape.
4. Remove supernatant (500 uL) immediately and place into a new tube.
5. Mix 500 ul of the supernatant with same volume of Phenol:Chloroform:Isoamyl Alcohol.
6. Vortex for 15 seconds.
7. Centrifuge for 5 min at 13000 rpm at the benchtop centrifuge.
8. Collect the top layer to a new tube and add 400 ul of Phenol:Chloroform:Isoamyl Alcohol.
9. Vortex for 15 seconds.
10. Centrifuge for 5 min at 13000 rpm.
11. Collect the top layer to a new tube and add 300 ul of Chloroform.
12. Vortex for 15 seconds.
13. Centrifuge for 5 min at 13000 rpm.
14. Collect the top layer to a new tube and follow the PROMEGA kit instructions from Technical manual[15] by adding IOOul of Isopropanol.
15. Vortex for 5 seconds.
16. Transfer the lysate to the minicolumn and centrifuge at 14,000 g for 30 secs.
17. Discard the flow through and place the minicolumn back into the collection tube.
18. Add 500 µl of RNA Wash Solution to the minicolumn.
19. Centrifuge at 14,000 g for 30 seconds.
20. Empty the collection tube.
21. In a sterile tube, prepare the DNase I incubation mix by combining 24 ul of Yellow Core Buffer, 3 ul of $MnCl_2$ and 3 ul of DNase I (per sample). Mix by gentle pipetting.
22. Apply 30 µl of the DNase I incubation mix directly to the membrane inside the column.
23. Incubate for 15 minutes at room temperature.
24. Add 200 µl of Column Wash Solution to the minicolumn.
25. Centrifuge at 14,000×g for 30 seconds. There is no need to empty the collection tube.
26. Add 500 µl of RNA Wash Solution.
27. Centrifuge at 14,000×g for 30 seconds.
28. Discard the collection tube and place the minicolumn into a new collection tube.
29. Add 300 µl of RNA Wash Solution.
30. Centrifuge at high speed for 2 minutes.
31. Transfer the minicolumn from the collection tube to the elution tube and add 60 ul of Nuclease-Free Water to the membrane.
32. Let it sit for 1 minute.
33. Centrifuge at 14,000×g for 1 minute at 4° C. Remove the column and discard. Cap the Elution Tube containing the purified RNA.
34. Centrifuge at 13,000×rpm for 3 minutes at 4° C. and transfer the supernatant to a new tube.
35. RNA can be quantified using intercalating dye kit (such as Qubit). Spectrophotometry has not been shown to be useful.

Guidance on Handling Low DNA and RNA Samples

Air-borne and contact contamination can be avoided during sample handling. Part of the contamination risk during the DNA and RNA extraction steps originates from human PCR amplicons. Thus, to reduce the risk, isolation and amplification steps can be performed in separate rooms. For example, a PCR room can be created to be equipped with separate stations for solvent- and kit-based RNA extractions, and pre-amplification steps, with exclusive equipment (vortex, centrifuges, and pipettes). Moreover, to ensure complete sterile environment, these stations can also be equipped with UV lights and HEPA filters. Cross contamination between reagents and samples can be reduced by using one time use aliquots of primers, water and reagents. Diluted Gene expression Taqman probes and Pyrosequencing primer sets can be stored in a separate −20° C. unit. DNA extraction and bisulfite conversion treatment can be performed in a separate room, where only genomic DNA is handled, and no PCR product is allowed. If any PCR product is to be handled, for example to be visualized in an agarose gel, it can be done in a separate lab bench area to avoid cross-contamination.

For quality control, appropriate positive and negative controls are used. For example, controls can include a PCR negative control (water only/no cDNA template control), reverse transcriptase negative control (water only/no RNA) and a No RT enzyme negative control, as well as a suitable positive control (cultured human keratinocytes, HaCat).

Downstream Application Methods

Shotgun Metagenomic Sequencing

DNA concentration was measured using Qubit®. Amplified library generation was performed with Nextera XT® adapters, and sequencing was performed to obtain 150 bp DNA paired end reads to a depth of 2.5 G base pairs per sample using an Illumina NextSeq500® machine. Raw sequence reads were extracted and demultiplexed using the Illumina program bcl2fastq. Raw reads were then filtered and trimmed for quality control using the program Sickle.[16] Trimmed reads were aligned using Kraken[17] to a custom microbial genome database An exact sequence read match of k-mer length 32 was used in Kraken to assign reads to the lowest common ancestor. Normalization of count data to the lowest number of total reads mapped among the samples was performed using rrarefy with the Vegan package in R to give the relative abundance at both the genus and species level 18. Principal component analysis was performed on a Euclidian distance matrix calculated from normalized species abundance data using the ade4 and Vegan packages in R. The machine learning algorithm, Random Forest, was used to identify key species that distinguish patient cohorts using the R packages randomForest and Boruta[19,20].

Bisulfite Pyrosequencing

For DNAm measurement, 20 ul of the tape genomic DNA was subjected to overnight sodium bisulfite treatment and purified using the EZ DNA methylation-Gold Kit (Zymo research, Irvine, CA, USA) according to the manufacturer's specifications. Pyrosequencing was carried out using Pyro Gold reagents with a PyroMark vacuum prep workstation and a PyroMark Q96 MD instrument (Qiagen, Valencia, CA, USA) following the manufacturer's instructions. The generated pyrograms were automatically analyzed using Pyro Q-CpG methylation analysis software (Qiagen, Valencia, CA, USA).

qRT-PCR 16 ul of RNA was used to perform reverse transcriptase reaction with the Superscript IV VILO Master Mix (Invitrogen). Negative and positive control sample were created at this point. The reaction was diluted 10 times and 6.75 ul was used for each PCR reaction. Taqman probes for GAPDH (Hs02786624_g1), FLG (Hs00856927_g1), LOR (Hs01894962_s1) and KRT14 (Hs00265033_m1) were used following the manufacturer's instructions.

Materials:

Collection
    Smartsolve, Bowling Green, OH; 1 in.×30 yd roll (catalog #IT112021S)
    BL+TG Buffer (4M Guanidine thiocyanate, 0.01 M Tris (pH 7.5), 2% 1-Thioglycerol)

DNA Isolation
    QIAamp BiOstic Bacteremia DNA Kit (catalog #12240-50)
    ZymoTaq DNA Polymerase Premix (catalog #E2004)
    EZ DNA Methylation-Gold Kit (catalog #D5006)

RNA Isolation
    Phenol:Chloroform:Isoamyl Alcohol (catalog #AM9722)
    Promega ReliaPrep™ RNA Cell Miniprep System (catalog #Z6012)

Gene Expression
    Superscript™ IV VILO™ Master Mix (catalog #11756500)
    GAPDH (Hs02786624_g1)
    FLG (Hs00856927_g1)
    LOR (Hs01894962_s1)
    KRT14 (Hs00265033_m1)
    Taqman Fast Advanced MasterMix (catalog #4444963)

Example 4: Comparison of Collection Techniques/Materials Trialed in Development of Method Several methods for minimally invasive skin collection have emerged over the past years 1-"3. For nucleic acid, protein and interstitial fluid collection from skin, methods include abrasion techniques[4], skin tape[4,11] or cyanoacrylate stripping, reverse iontophoresis[4], and ultrasound-based methods. Similarly, sampling the skin with Q-tips, gauze or skin tape has been a reliable way to sample microbiome.

Different types of strips (water-soluble strips vs. water-insoluble strips) were tested for DNA/RNA isolation and yields were compared (see Table 1). The Smartsolve tape is water soluble, while the other tapes, Tegaderm dressing, Transpore surgical tape, Blenderm surgical tape, Cytology Brush, Sheer bandage, and fabric bandage are all water insoluble. The criteria used to assess the tapes for minimally invasive collection technique are shown in Table 2.

Figure 11:
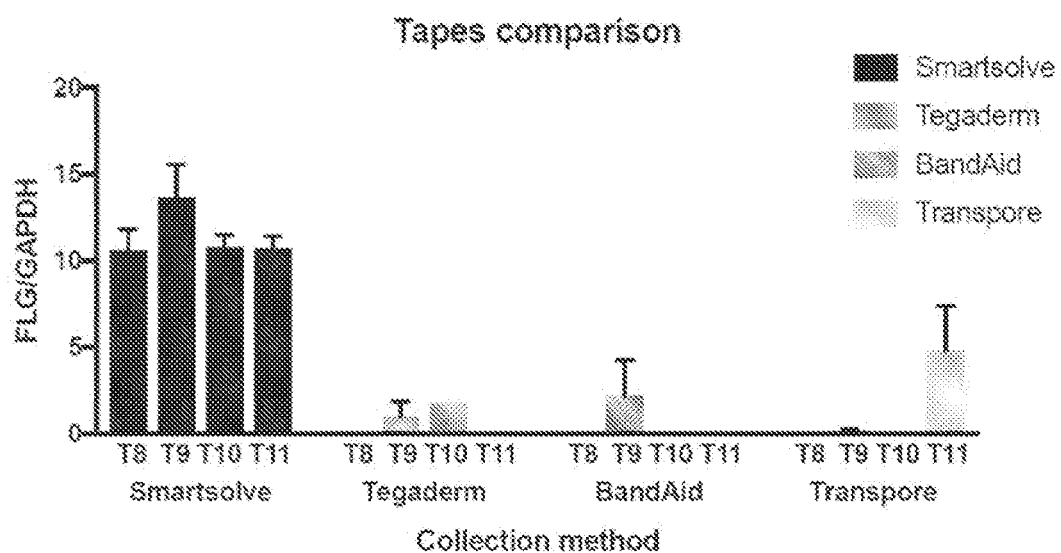
FIG. 11 is a diagram showing quantitative results of FLG expression (normalized to GAPDH expression) from RNA collected from skin using adhesives tapes of different materials. Water-soluble adhesive tapes (Smartsolve®) show higher RNA yield than other water-insoluble adhesive tapes (Tegaderm®, BandAid®, and Transpore®).

FIG. 11 shows quantitative results of FLG expression (normalized to GAPDH expression) from RNA collected from skin using adhesives tapes of different materials. Water-soluble adhesive tapes (Smartsolve®) show higher RNA yield than other water-insoluble adhesive tapes (Tegaderm®, BandAid®, and Transpore®).

TABLE 1

Comparison of collection techniques/materials trialed in development of method

| Material | Company | RNA isolation success | Ease of use (by collector and processing) | Tolerability (rash, pain) | Cost | Comments |
| --- | --- | --- | --- | --- | --- | --- |
| Tegaderm dressing | 3M | − | + | + | $$$ | Flimsy, easily rips and adheres to self |
| Transpore surgical tape | 3M | − | + | + | $$$ | Hard to precut, tape too rigid and adhesive too strong |
| Blenderm surgical tape | 3M | − | + | + | $$$ | Hard to precut, Too rigid and adhesive too strong |

TABLE 1-continued

Comparison of collection techniques/materials trialed in development of method

| Material | Company | RNA isolation success | Ease of use (by collector and processing) | Tolerability (rash, pain) | Cost | Comments |
|---|---|---|---|---|---|---|
| Cytology Brush | Medical Packaging Corp | − | + | ++ | $ | Brush rubbed on skin, very inconsistent |
| Smartsolve water soluble tape | Smartsolve | +++ | ++ | ++ | $ | Easy to precut, tape disintegrates in buffer |
| Sheer bandage | Kroger | + | + | + | $ | Easy to precut, only adhesive portion used |
| Fabric bandage | Kroger | + | + | + | $ | Easy to precut, only adhesive portion used |

TABLE 2

Criteria used to assess materials for minimally invasive collection technique.

Tolerability by subject
  Rash
  Pain
Ease of use by collector
  Peel off backing to allow precutting tape strips
  Rigidness of tape (ability to easily put into tube)
  Adhesive strength (ability to remove from skin)
Cost
Ease of processing sample
Usability of nucleic acid (specifically RNA)
  RNA yield based on Qubit and/or qPCR

REFERENCES

1 Barash, M., Reshef, A. & Brauner, P. The use of adhesive tape for recovery of DNA from crime scene items. J Forensic Sci 55, 1058-1064, doi: 10.1111/j.1556-4029.2010.01416.x (2010).

2 Kopka, J., Leder, M., Jaureguiberry, S. M., Brem, G. & Boselli, G. O. New optimized DNA extraction protocol for fingerprints deposited on a special self-adhesive security seal and other latent samples used for human identification. J Forensic Sci 56, 1235-1240, doi: 10.1111/j.1556-4029.2011.01853.x (2011).

3 Paliwal, S., Ogura, M. & Mitragotri, S. Rapid Sampling of Molecules via Skin for Diagnostic and Forensic Applications. Pharmaceutical Research 27, 1255-1263, doi: 10.1007/s 11095-010-0081-2 (2010).

4 Wang, C. Y. & Maibach, H. I. Why minimally invasive skin sampling techniques? A bright scientific future. Cutaneous and ocular toxicology 30, 1-6, doi: 10.3109/15569527.2010.517230 (2011).

5 Benson, N. R. et al. An analysis of select pathogenic messages in lesional and non-lesional psoriatic skin using non-invasive tape harvesting. The Journal of investigative dermatology 126, 2234-2241, doi: 10.1038/sj.jid.5700412 (2006).

6 Clausen, M. L., Slotved, H. C, Krogfelt, K. A. & Agner, T. Tape Stripping Technique for Stratum Corneum Protein Analysis. Sci Rep 6, 8, doi: 10.1038/srep19918 (2016).

7 Emson, C. L. et al. A pilot study demonstrating a non-invasive method for the measurement of protein turnover in skin disorders: application to psoriasis. Clinical and translational medicine 2, 12, doi: 10.1186/2001-1326-2-12 (2013).

8 Morhenn, V. B., Chang, E. Y. & Rheins, L. A. A noninvasive method for quantifying and distinguishing inflammatory skin reactions. Journal of the American Academy of Dermatology 41, 687-692 (1999).

9 Wachsman, W. et al. Noninvasive genomic detection of melanoma. The British journal of dermatology 164, 797-806, doi: 10.1111/j.1365-2133.2011.10239.x (2011).

10 Wong, R. et al. Use of RT-PCR and DNA microarrays to characterize RNA recovered by non-invasive tape harvesting of normal and inflamed skin. The Journal of investigative dermatology 123, 159-167, doi: 10.1111/j.0022-202X.2004.22729.x (2004).

11 Wong, R., Tran, V., Talwalker, S. & Benson, N. R. Analysis of RNA recovery and gene expression in the epidermis using non-invasive tape stripping. Journal of dermatological science 44, 81-92, doi: 10.1016/j.jdermsci.2006.08.007 (2006).

12 Lecomte, M. M. J., Atkinson, K. R., Kay, D. P., Simons, J. L. & Ingram, J. R. A modified method using the SonoPrep® ultrasonic skin permeation system for sampling human interstitial fluid is compatible with proteomic techniques. Skin Res. Technol. 19, 27-34, doi: 10.1111/j.1600-0846.2012.00641.x (2013).

13 Harder, J. & Schroder, J. M. RNase 7, a novel innate immune defense antimicrobial protein of healthy human skin. J Biol Chem 277, 46779-46784, doi: 10.1074/jbc.M207587200 (2002).

14 Fischer, H. et al. DNase 2 is the main DNA-degrading enzyme of the stratum corneum. PLoS One 6, e17581, doi: 10.1371/journal.pone.0017581 (2011).

15 Promega. in Promega Website (2012).

16 Joshi, N. Sickle: A sliding-window, adaptive, quality-based trimming tool for FastQ files. (2011).

17 Wood, D. E. & Salzberg, S. L. Kraken: ultrafast metagenomic sequence classification using exact alignments. Genome biology 15, R46, doi: 10.1186/gb-2014-15-3-r46 (2014).

18 Oksanen, J. et al. vegan: Community Ecology Package version 2.3-0. (2015).

19 Liaw, A. & Wiener, M. Classification and Regression by randomForest. R News 2, 18-22 (2002).

20 Kursa, M. B. & Rudnicki, W. R. Feature Selection with the Boruta Package. The Journal of Statistical Software 36 (2010).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document. The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A kit for assessing a skin condition of a subject, the kit comprising:
   (a) a first set of adhesive tapes adapted to adhere a first biological material from stratum corneum of a target skin site of the subject,
   (b) a second set of adhesive tapes adapted to adhere a second biological material from an epidermis layer below stratum corneum of a target skin site of the subject, wherein each of the adhesive tapes in the first set of adhesive tapes and the second set of adhesive tapes comprises a water-soluble adhesive layer attached to a substrate,
   (c) one or more reagents for extracting biological material adhered to the water-soluble adhesive layers of the adhesive tapes, and
   (d) one or more detection agents for determining a presence of microbial biological materials and/or host biological materials from water-soluble adhesive tape extract.

2. The kit of claim 1, further comprising a third set of adhesive tapes, wherein each of the adhesive tapes in the third set of adhesive tapes is adapted to adhere biological material from an epidermis layer below stratum corneum, wherein each of the adhesive tapes in the third set of adhesive tapes comprises a water-soluble adhesive layer attached to a substrate.

3. The kit of claim 1, wherein the first set of the adhesive tapes and/or the second set of the adhesive tapes each contain 2-10 tapes.

4. The kit of claim 1, wherein the first set of the adhesive tapes and the second set of the adhesive tapes each contain 2-5 tapes.

5. The kit of claim 1, wherein the substrate of the adhesive tapes in the first set of adhesive tapes and the second set of adhesive tapes is a water-soluble substrate.

6. The kit of claim 5, wherein the water-soluble substrate comprises cellulose.

7. The kit of claim 1, wherein the water-soluble adhesive layer in the adhesive tapes of the first set of adhesive tapes and the second set of adhesive tapes comprises a water-soluble polymer.

8. The kit of claim 7, wherein the water-soluble polymer comprises water soluble acrylic acid polymer, acrylic acid ester/acrylic acid copolymer, carboxymethyl starch, polyvinyl alcohol, cellulose ether, methylcellulose polymer, carboxymethylcellulose, polyvinylpyrrolidone, glutin adhesive, starch adhesive, casein adhesive, or a combination of two or more thereof.

9. The kit of claim 7, wherein the water-soluble polymer comprises a water-soluble acrylic polymer.

10. The kit of claim 1, wherein the one or more reagents for extracting biological material comprises an aqueous buffer solution or a buffer agent for forming an aqueous buffer solution.

11. The kit of claim 1, wherein the one or more reagents for extracting biological material comprises tris(hydroxymethyl)aminomethane), glycerol, thioglycerol, and/or guanidinium thiocyanate.

12. The kit of claim 1, wherein the one or more reagents for extracting biological material comprises tris(hydroxymethyl)aminomethane), thioglycerol, and guanidinium thiocyanate.

13. The kit of claim 1, wherein the one or more reagents for extracting biological material comprises guanidinium thiocyanate.

14. The kit of claim 1, wherein the one or more detection agents comprises a microbial culture medium, an agent for detecting microorganisms, an agent for detecting host biological materials, or a combination thereof.

15. The kit of claim 1, wherein the one or more detection agents comprises oligonucleotide primers and probes and DNA polymerase for amplification and/or detection of a gene of interest.

16. The kit of claim 15, wherein the oligonucleotide primers and probes are adapted for amplifying and/or detecting one or more housekeeping genes, keratinocyte-specific genes, and/or atopic dermatitis-related genes.

17. The kit of claim 15, wherein the oligonucleotide primers and probes are adapted for amplifying and detecting genes expressing one or more of glyceraldehyde 3-phosphate dehydrogenase (GAPDH), filaggrin (FLG), loricrin (LOR), Keratin1, Keratin14 (KRT14), Claudin1 (CLD1), Cadherin (CDH), S100A8, S100A9, and KIF3A.

18. The kit of claim 1, wherein the one or more detection agents comprises a capture antibody for atopic dermatitis-related protein or peptide.

19. The kit of claim 1, wherein the one or more detection agents comprises (i) an agent for preparing a microbial DNA library; and (ii) an agent for detecting the presence of epidermal DNA, epidermal RNA, or epidermal lipid, or agents for detecting the presence of epidermal DNA and epidermal RNA, or agents for or detecting the presence of epidermal DNA, epidermal RNA, and epidermal lipid.

20. The kit of claim 19, wherein the agent for preparing a microbial DNA library is adapted for metagenomic shotgun sequencing or for 16S rRNA sequencing.

* * * * *

SEQUENCE LISTING

```
Sequence total quantity: 2
SEQ ID NO: 1          moltype = DNA  length = 29
FEATURE               Location/Qualifiers
source                1..29
                      mol_type = genomic DNA
                      organism = Homo sapiens
```

```
SEQUENCE: 1
ttcgtatagg ataaaaaata ttgtattaa                                          29

SEQ ID NO: 2            moltype = DNA  length = 29
FEATURE                 Location/Qualifiers
modified_base           3
                        mod_base = OTHER
                        note = methylated cytosine
source                  1..29
                        mol_type = genomic DNA
                        organism = Homo sapiens
SEQUENCE: 2
ttcgtatagg ataaaaaata ttgtattaa                                          29
```